US008029488B2

(12) United States Patent
Ashton et al.

(10) Patent No.: US 8,029,488 B2
(45) Date of Patent: Oct. 4, 2011

(54) DISPOSABLE PULL-ON DIAPER HAVING A LOW FORCE, SLOW RECOVERY ELASTIC WAIST

(75) Inventors: Gregory Ashton, Cincinnati, OH (US); Eiro Fukuda, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 319 days.

(21) Appl. No.: 11/340,803

(22) Filed: Jan. 26, 2006

(65) Prior Publication Data
US 2006/0167434 A1 Jul. 27, 2006

Related U.S. Application Data

(60) Provisional application No. 60/647,246, filed on Jan. 26, 2005.

(51) Int. Cl.
*A61F 13/15* (2006.01)
(52) U.S. Cl. .......... 604/385.24; 604/396; 604/392; 604/385.3; 604/385.29
(58) Field of Classification Search ............. 604/392, 604/396, 385.24, 385.3, 385.29
See application file for complete search history.

(56) References Cited

U.S. PATENT DOCUMENTS

| 3,086,242 A | 4/1963 | Cook et al. |
| 3,139,468 A | 6/1964 | Wheat |
| 3,370,630 A | 2/1968 | Gordon et al. |
| 3,587,581 A * | 6/1971 | Jones, Sr. ............ 604/402 |
| 3,592,946 A | 7/1971 | Griffith |
| 3,601,923 A | 8/1971 | Rosenberg |
| 3,639,917 A | 2/1972 | Althouse |
| 3,673,280 A * | 6/1972 | Minton et al. ............ 525/279 |
| 3,819,401 A | 6/1974 | Massengale et al. |
| 3,848,594 A | 11/1974 | Buell |
| 3,860,003 A | 1/1975 | Buell |
| 3,911,173 A | 10/1975 | Sprague, Jr. |
| 3,912,565 A | 10/1975 | Koch et al. |
| 3,929,135 A | 12/1975 | Thompson |

(Continued)

FOREIGN PATENT DOCUMENTS

CH 528285 2/1968

(Continued)

OTHER PUBLICATIONS

Ziabicki, *Fundamentals of Fibre Formation*, John Wiley & Sons, New York (1976), Chapter 6.

(Continued)

*Primary Examiner* — Jacqueline F Stephens
(74) *Attorney, Agent, or Firm* — John G. Powell; Kathleen Y. Carter; Richard L. Alexander

(57) ABSTRACT

A disposable pull-on diaper having a wearer-facing surface and a garment-facing surface; a longitudinal centerline and a lateral centerline; a front waist region, a back waist region, and a crotch region disposed between the front and back waist regions. The front waist region and back waist region of the pull-on diaper interconnect to form a waist opening and leg openings. The pull-on diaper includes an absorbent assembly and an elastic belt. The absorbent assembly includes a liquid pervious topsheet, a liquid impervious backsheet, and an absorbent core disposed between the topsheet and backsheet. The elastic belt may exhibit less than about 80% of the maximum force after 15 seconds as measured by the Percent Release Test.

19 Claims, 8 Drawing Sheets

U.S. PATENT DOCUMENTS

| | | | |
|---|---|---|---|
| RE28,688 E | 1/1976 | Cook | |
| 4,054,616 A | 10/1977 | Miki et al. | |
| 4,089,913 A | 5/1978 | Miki et al. | |
| 4,097,425 A * | 6/1978 | Niznik | 521/90 |
| 4,116,842 A | 9/1978 | Meier | |
| 4,122,134 A | 10/1978 | Miki et al. | |
| 4,152,370 A | 5/1979 | Moczygemba | |
| 4,169,336 A | 10/1979 | Kuhn | |
| 4,248,981 A | 2/1981 | Milkovich et al. | |
| 4,248,982 A | 2/1981 | Bi et al. | |
| 4,248,984 A | 2/1981 | Bi et al. | |
| 4,259,220 A | 3/1981 | Bunnelle et al. | |
| 4,324,246 A | 4/1982 | Mullane et al. | |
| 4,337,771 A * | 7/1982 | Pieniak et al. | 604/370 |
| 4,342,314 A | 8/1982 | Radel et al. | |
| 4,346,198 A | 8/1982 | Doak et al. | |
| 4,381,781 A | 5/1983 | Sciaraffa et al. | |
| 4,412,087 A | 10/1983 | Trepka | |
| 4,418,123 A * | 11/1983 | Bunnelle et al. | 428/517 |
| 4,418,180 A | 11/1983 | Heinz et al. | |
| 4,450,026 A | 5/1984 | Pieniak et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,603,155 A | 7/1986 | Muramori et al. | |
| 4,609,191 A | 9/1986 | Remme | |
| 4,610,678 A | 9/1986 | Weisman et al. | |
| 4,629,643 A | 12/1986 | Curro et al. | |
| 4,636,207 A | 1/1987 | Buell | |
| 4,662,875 A | 5/1987 | Hirotsu et al. | |
| 4,673,402 A | 6/1987 | Weisman et al. | |
| 4,681,580 A | 7/1987 | Reising et al. | |
| 4,695,278 A | 9/1987 | Lawson | |
| 4,698,242 A * | 10/1987 | Salerno | 427/208.2 |
| 4,699,622 A | 10/1987 | Toussant et al. | |
| 4,699,941 A | 10/1987 | Salerno | |
| 4,704,115 A | 11/1987 | Buell | |
| 4,704,116 A | 11/1987 | Enloe | |
| 4,704,434 A | 11/1987 | Kitchen et al. | |
| 4,710,189 A | 12/1987 | Lash | |
| 4,719,261 A | 1/1988 | Bunnelle et al. | |
| 4,720,415 A | 1/1988 | Vander Wielen et al. | |
| 4,761,198 A | 8/1988 | Salerno | |
| 4,785,996 A | 11/1988 | Ziecker et al. | |
| 4,787,897 A | 11/1988 | Torimae et al. | |
| 4,795,454 A | 1/1989 | Dragoo | |
| 4,808,178 A | 2/1989 | Aziz et al. | |
| 4,813,947 A * | 3/1989 | Korpman | 604/387 |
| 4,816,025 A | 3/1989 | Foreman | |
| 4,816,094 A | 3/1989 | Pomplun et al. | |
| 4,820,590 A | 4/1989 | Hodgson, Jr. et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,874,255 A | 10/1989 | Ball et al. | |
| 4,888,231 A | 12/1989 | Angstadt | |
| 4,892,536 A | 1/1990 | Desmarais et al. | |
| 4,894,060 A | 1/1990 | Nestegard | |
| 4,900,317 A | 2/1990 | Buell | |
| 4,909,803 A | 3/1990 | Aziz et al. | |
| 4,938,753 A | 7/1990 | Van Gompel et al. | |
| 4,939,208 A | 7/1990 | Lanza et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,968,312 A | 11/1990 | Khan | |
| 4,981,747 A | 1/1991 | Morman | |
| 4,987,194 A | 1/1991 | Maeda et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,026,364 A | 6/1991 | Robertson | |
| 5,028,646 A | 7/1991 | Miller et al. | |
| 5,036,978 A | 8/1991 | Frank et al. | |
| 5,037,416 A | 8/1991 | Allen et al. | |
| 5,047,484 A | 9/1991 | Tung | |
| 5,049,591 A | 9/1991 | Hayashi et al. | |
| 5,050,742 A | 9/1991 | Muckenfuhs | |
| 5,054,619 A | 10/1991 | Muckenfuhs | |
| 5,062,840 A | 11/1991 | Holt et al. | |
| 5,085,654 A | 2/1992 | Buell | |
| 5,089,558 A | 2/1992 | Hall et al. | |
| 5,092,861 A | 3/1992 | Nomura et al. | |
| 5,093,384 A | 3/1992 | Hayashi et al. | |
| 5,098,776 A | 3/1992 | Kobayashi et al. | |
| 5,114,763 A * | 5/1992 | Brant et al. | 428/34.9 |
| 5,114,781 A | 5/1992 | Morman | |
| 5,116,662 A | 5/1992 | Morman | |
| 5,118,762 A | 6/1992 | Chin | |
| 5,135,786 A | 8/1992 | Hayashi et al. | |
| 5,137,537 A | 8/1992 | Herron et al. | |
| 5,139,832 A | 8/1992 | Hayashi et al. | |
| 5,145,935 A | 9/1992 | Hayashi | |
| 5,147,345 A | 9/1992 | Young et al. | |
| 5,149,741 A | 9/1992 | Alper et al. | |
| 5,151,092 A | 9/1992 | Buell et al. | |
| 5,156,793 A | 10/1992 | Buell et al. | |
| 5,156,911 A | 10/1992 | Stewart | |
| 5,159,022 A | 10/1992 | Ikematu et al. | |
| 5,167,897 A | 12/1992 | Weber et al. | |
| 5,171,236 A | 12/1992 | Dreier et al. | |
| 5,188,627 A | 2/1993 | Igaue et al. | |
| 5,189,110 A | 2/1993 | Ikematu et al. | |
| 5,192,301 A | 3/1993 | Kamiya et al. | |
| 5,221,274 A | 6/1993 | Buell et al. | |
| 5,226,992 A | 7/1993 | Morman | |
| 5,234,999 A | 8/1993 | Tung et al. | |
| 5,242,436 A | 9/1993 | Weil et al. | |
| 5,246,433 A | 9/1993 | Hasse et al. | |
| 5,256,736 A | 10/1993 | Trepka et al. | |
| 5,260,345 A | 11/1993 | Desmarais et al. | |
| 5,269,755 A | 12/1993 | Bodicky | |
| 5,270,388 A | 12/1993 | Onishi et al. | |
| 5,296,184 A | 3/1994 | Wu | |
| 5,306,266 A | 4/1994 | Freeland | |
| 5,336,545 A | 8/1994 | Morman | |
| 5,342,338 A | 8/1994 | Roe | |
| 5,344,691 A * | 9/1994 | Hanschen et al. | 428/152 |
| 5,358,500 A | 10/1994 | LaVon et al. | |
| 5,358,783 A | 10/1994 | Diehl et al. | |
| 5,387,207 A | 2/1995 | Dyer et al. | |
| 5,387,450 A | 2/1995 | Stewart | |
| 5,397,316 A | 3/1995 | LaVon et al. | |
| 5,397,318 A | 3/1995 | Dreier | |
| 5,429,856 A | 7/1995 | Krueger et al. | |
| 5,439,459 A | 8/1995 | Tanji et al. | |
| 5,439,966 A | 8/1995 | Graham et al. | |
| 5,445,140 A | 8/1995 | Tovey | |
| 5,447,508 A | 9/1995 | Numano et al. | |
| 5,468,237 A | 11/1995 | Miller et al. | |
| 5,468,428 A * | 11/1995 | Hanschen et al. | 264/483 |
| 5,492,751 A | 2/1996 | Butt, Sr. et al. | |
| 5,499,978 A | 3/1996 | Buell et al. | |
| 5,506,300 A | 4/1996 | Ward et al. | |
| 5,507,736 A | 4/1996 | Clear et al. | |
| 5,514,121 A | 5/1996 | Roe et al. | |
| 5,518,433 A | 5/1996 | Sneddon | |
| 5,518,801 A | 5/1996 | Chappell et al. | |
| 5,536,563 A * | 7/1996 | Shah et al. | 442/329 |
| 5,540,671 A | 7/1996 | Dreier | |
| 5,540,976 A | 7/1996 | Shawver et al. | |
| 5,545,690 A | 8/1996 | Trepka et al. | |
| 5,554,145 A | 9/1996 | Roe et al. | |
| 5,559,165 A * | 9/1996 | Paul | 523/111 |
| 5,569,234 A | 10/1996 | Buell et al. | |
| 5,571,096 A | 11/1996 | Dobrin et al. | |
| 5,580,411 A | 12/1996 | Nease et al. | |
| H1630 H | 1/1997 | Roe et al. | |
| 5,591,152 A | 1/1997 | Buell et al. | |
| 5,607,760 A | 3/1997 | Roe | |
| 5,609,587 A | 3/1997 | Roe | |
| 5,620,780 A * | 4/1997 | Krueger et al. | 428/179 |
| 5,625,222 A | 4/1997 | Yoneda et al. | |
| 5,634,913 A | 6/1997 | Stinger | |

| | | | | | | |
|---|---|---|---|---|---|---|
| 5,635,191 | A | 6/1997 | Roe et al. | 6,571,704 B2 | 6/2003 | Fujimoto et al. |
| H1670 | H | 7/1997 | Aziz et al. | 6,579,940 B1 | 6/2003 | Dove |
| 5,643,588 | A | 7/1997 | Roe et al. | 6,592,995 B2 | 7/2003 | Topolkaraev et al. |
| 5,648,167 | A | 7/1997 | Peck | 6,593,430 B1 | 7/2003 | Knoll et al. |
| 5,653,703 | A | 8/1997 | Roe et al. | 6,598,637 B2 | 7/2003 | Lechtenböhmer et al. |
| 5,669,897 | A | 9/1997 | Lavon et al. | 6,626,879 B1 | 9/2003 | Ashton et al. |
| 5,691,034 | A | 11/1997 | Krueger et al. | 6,627,673 B2 | 9/2003 | Topolkaraev et al. |
| 5,714,548 | A | 2/1998 | Ma et al. | 6,635,041 B1 | 10/2003 | Popp et al. |
| 5,719,226 | A | 2/1998 | Kegley | 6,648,869 B1 | 11/2003 | Gillies et al. |
| H1732 | H | 6/1998 | Johnson | 6,657,000 B1 | 12/2003 | De Keyzer et al. |
| 5,762,641 | A | 6/1998 | Bewick-Sonntag et al. | 6,664,309 B2 | 12/2003 | Svenningsen et al. |
| 5,814,705 | A | 9/1998 | Ward et al. | 6,664,436 B2 | 12/2003 | Topolkaraev et al. |
| 5,830,203 | A | 11/1998 | Suzuki et al. | 6,673,857 B1 | 1/2004 | Knoll et al. |
| 5,853,864 | A | 12/1998 | Bunnelle | H2100 | H | 4/2004 | Hansen et al. |
| 5,858,150 | A | 1/1999 | Yarusso et al. | 6,722,910 B2 | 4/2004 | Kajinuma |
| 5,865,823 | A | 2/1999 | Curro | 6,746,433 B1 | 6/2004 | Shimoe et al. |
| 5,889,118 | A | 3/1999 | Delgado et al. | 6,759,454 B2 | 7/2004 | Stephens et al. |
| 5,897,545 | A | 4/1999 | Kline et al. | 6,759,481 B2 | 7/2004 | Tong |
| 5,899,895 | A | 5/1999 | Robles et al. | 6,790,911 B2 | 9/2004 | Perevosnik et al. |
| 5,910,546 | A | 6/1999 | Trepka et al. | 6,818,093 B1 | 11/2004 | Taal et al. |
| 5,916,206 | A | 6/1999 | Otsubo et al. | 6,827,806 B2 | 12/2004 | Uitenbroek et al. |
| 5,934,470 | A | 8/1999 | Bauer et al. | 6,844,383 B2 | 1/2005 | Hoshi et al. |
| 5,938,648 | A | 8/1999 | LaVon et al. | 6,887,916 B2 | 5/2005 | Zhou et al. |
| 5,941,864 | A | 8/1999 | Roe | 6,933,421 B2 | 8/2005 | Topolkaraev et al. |
| 5,957,908 | A | 9/1999 | Kline et al. | 6,939,906 B2 | 9/2005 | Hoshi et al. |
| 5,968,025 | A | 10/1999 | Roe et al. | 6,946,172 B2 | 9/2005 | Munn et al. |
| 5,972,519 | A | 10/1999 | Niessner et al. | 6,967,178 B2 | 11/2005 | Zhou et al. |
| 5,977,430 | A | 11/1999 | Roe et al. | 6,969,441 B2 | 11/2005 | Welch et al. |
| 5,997,520 | A | 12/1999 | Ahr et al. | 6,978,486 B2 | 12/2005 | Zhou et al. |
| 6,004,306 | A | 12/1999 | Robles et al. | 7,015,155 B2 | 3/2006 | Zhou et al. |
| 6,010,490 | A | 1/2000 | Freeland et al. | 7,056,411 B2 | 6/2006 | Desai et al. |
| 6,013,063 | A | 1/2000 | Roe et al. | 7,074,484 B2 | 7/2006 | Topolkaraev et al. |
| 6,025,071 | A | 2/2000 | Cameron et al. | 7,087,287 B2 | 8/2006 | Curro et al. |
| 6,031,053 | A | 2/2000 | Knoll et al. | 7,223,261 B2 | 5/2007 | Müeller et al. |
| 6,063,838 | A | 5/2000 | Patnode et al. | 7,316,840 B2 | 1/2008 | Neculescz et al. |
| 6,103,814 | A | 8/2000 | Vandrongelen et al. | 7,316,842 B2 | 1/2008 | Zhou et al. |
| 6,107,537 | A | 8/2000 | Elder et al. | 2001/0004689 A1 | 6/2001 | Otsubo |
| 6,120,487 | A | 9/2000 | Ashton | 2002/0056384 A1 | 5/2002 | Fujimoto et al. |
| 6,120,489 | A | 9/2000 | Johnson et al. | 2002/0096072 A1 | 7/2002 | Fujimoto et al. |
| 6,120,866 | A | 9/2000 | Arakawa et al. | 2002/0115744 A1 | 8/2002 | Svenningsen et al. |
| 6,140,433 | A | 10/2000 | Zhang et al. | 2002/0115772 A1 | 8/2002 | Topolkaraev et al. |
| 6,149,637 | A | 11/2000 | Allen et al. | 2002/0115977 A1 | 8/2002 | Topolkaraev et al. |
| 6,156,842 | A | 12/2000 | Hoenig et al. | 2002/0143313 A1 | 10/2002 | Tsuji et al. |
| 6,168,584 | B1 | 1/2001 | Allen et al. | 2002/0147273 A1 | 10/2002 | Patel et al. |
| 6,177,517 | B1 | 1/2001 | Guntherberg et al. | 2002/0165516 A1* | 11/2002 | Datta et al. ............... 604/385.16 |
| 6,179,820 | B1 | 1/2001 | Fernfors | 2003/0088228 A1 | 5/2003 | Desai et al. |
| 6,184,285 | B1 | 2/2001 | Goodman et al. | 2003/0091807 A1 | 5/2003 | Desai et al. |
| 6,187,696 | B1 | 2/2001 | Lim et al. | 2003/0111166 A1 | 6/2003 | Uitenbroek et al. |
| 6,190,768 | B1 | 2/2001 | Turley et al. | 2003/0120240 A1* | 6/2003 | Buell et al. ............... 604/385.01 |
| 6,193,701 | B1 | 2/2001 | Van Gompel et al. | 2003/0171464 A1* | 9/2003 | Corzani et al. ............... 524/115 |
| 6,194,073 | B1 | 2/2001 | Li et al. | 2003/0233082 A1 | 12/2003 | Kline et al. |
| 6,197,889 | B1 | 3/2001 | Knoll et al. | 2004/0005832 A1 | 1/2004 | Zhou et al. |
| 6,211,272 | B1 | 4/2001 | Hansen et al. | 2004/0005834 A1 | 1/2004 | Zhou et al. |
| 6,235,847 | B1 | 5/2001 | Hoshi et al. | 2004/0005835 A1 | 1/2004 | Zhou et al. |
| 6,245,050 | B1 | 6/2001 | Odorzynski et al. | 2004/0006324 A1 | 1/2004 | Zhou et al. |
| 6,265,484 | B1 | 7/2001 | Trepka et al. | 2004/0013852 A1 | 1/2004 | Curro et al. |
| 6,265,485 | B1 | 7/2001 | Trepka et al. | 2004/0092900 A1 | 5/2004 | Hoffman et al. |
| 6,274,666 | B1 | 8/2001 | Dougherty | 2004/0092902 A1 | 5/2004 | Hoffman |
| 6,274,685 | B2 | 8/2001 | Blok et al. | 2004/0123938 A1 | 7/2004 | Zhou et al. |
| 6,288,149 | B1 | 9/2001 | Kroll | 2004/0127881 A1 | 7/2004 | Stevens et al. |
| 6,300,208 | B1 | 10/2001 | Talwar et al. | 2004/0162536 A1 | 8/2004 | Becker |
| 6,310,154 | B1 | 10/2001 | Babcock et al. | 2004/0162538 A1 | 8/2004 | Mueller |
| 6,357,499 | B1 | 3/2002 | Kralevich, Jr. et al. | 2004/0167486 A1 | 8/2004 | Busam |
| 6,369,160 | B1 | 4/2002 | Knoll et al. | 2004/0181200 A1 | 9/2004 | Desai et al. |
| 6,372,853 | B1 | 4/2002 | Li et al. | 2004/0182499 A1 | 9/2004 | Zhou et al. |
| 6,383,431 | B1 | 5/2002 | Dobrin et al. | 2004/0193134 A1 | 9/2004 | Mueller et al. |
| 6,418,848 | B1 | 7/2002 | Fujimoto et al. | 2004/0222553 A1 | 11/2004 | Desai et al. |
| 6,419,798 | B1 | 7/2002 | Topolkaraev et al. | 2005/0095942 A1 | 5/2005 | Mueller |
| 6,423,807 | B1 | 7/2002 | Oi et al. | 2005/0096416 A1 | 5/2005 | Zhou et al. |
| 6,432,098 | B1 | 8/2002 | Kline et al. | 2005/0170729 A1 | 8/2005 | Stadelman et al. |
| 6,444,755 | B1 | 9/2002 | Deporter et al. | 2005/0171499 A1 | 8/2005 | Nigam et al. |
| 6,455,627 | B1 | 9/2002 | De Keyzer et al. | 2005/0177123 A1 | 8/2005 | Catalan |
| 6,476,288 | B1 | 11/2002 | VanRijswijck et al. | 2005/0181207 A1* | 8/2005 | He et al. ............... 428/394 |
| 6,482,191 | B1 | 11/2002 | Roe et al. | 2005/0182183 A1* | 8/2005 | He et al. ............... 524/515 |
| 6,485,557 | B1 | 11/2002 | Swiler | 2005/0211368 A1 | 9/2005 | McGuire |
| 6,521,704 | B1 | 2/2003 | Hubbard et al. | 2005/0215901 A1* | 9/2005 | Anderson et al. ............... 600/445 |
| 6,531,544 | B1 | 3/2003 | Vaughan et al. | 2005/0215963 A1 | 9/2005 | Autran et al. |
| 6,533,987 | B2 | 3/2003 | Topolkaraev et al. | 2005/0215972 A1 | 9/2005 | Roe et al. |
| 6,565,549 | B1 | 5/2003 | Allen et al. | 2005/0215973 A1 | 9/2005 | Roe et al. |

| | | | | | | |
|---|---|---|---|---|---|---|
| 2005/0256476 | A1 | 11/2005 | Mirle et al. | JP | 8281764 | 10/1996 |
| 2005/0273071 | A1* | 12/2005 | McKiernan et al. ..... 604/385.24 | JP | 9291265 | 11/1997 |
| 2005/0273072 | A1* | 12/2005 | Hird et al. ................ 604/385.24 | JP | 9302319 | 11/1997 |
| 2006/0003656 | A1 | 1/2006 | Morman | JP | 2000282006 | 5/1999 |
| 2006/0004342 | A1 | 1/2006 | Sawyer et al. | JP | 11279521 | 10/1999 |
| 2006/0058765 | A1 | 3/2006 | Mueller | JP | 2001040302 | 2/2001 |
| 2006/0078042 | A1 | 4/2006 | Lee | JP | 2001279212 | 10/2001 |
| 2006/0083900 | A1 | 4/2006 | Ashraf | JP | 2001293789 | 10/2001 |
| 2006/0155255 | A1* | 7/2006 | McKiernan et al. ..... 604/385.24 | WO | WO 94/14395 | 7/1994 |
| 2006/0264858 | A1* | 11/2006 | Roe et al. ..................... 604/361 | WO | WO 95/16746 | 6/1995 |
| 2007/0037907 | A9 | 2/2007 | Zhou et al. | WO | WO 96/11236 | 4/1996 |
| 2007/0088307 | A1 | 4/2007 | Arizti | WO | WO 96/23823 | 8/1996 |
| 2007/0093771 | A1 | 4/2007 | Arizti | WO | WO 98/08476 | 3/1998 |
| 2007/0191806 | A1 | 8/2007 | Mueller | WO | WO 99/13016 | 3/1999 |
| 2007/0197993 | A1 | 8/2007 | Arizti | WO | WO 00/12645 | 3/2000 |
| 2007/0197994 | A1 | 8/2007 | Arizti | WO | WO 00/22061 | 4/2000 |
| 2008/0033388 | A1 | 2/2008 | Mueller | WO | WO 00/30581 A | 6/2000 |
| 2008/0108963 | A1 | 5/2008 | Ashton et al. | WO | WO 00/69834 A | 11/2000 |
| 2008/0195070 | A1 | 8/2008 | Ponomarenko et al. | WO | WO 01/19920 | 3/2001 |
| 2010/0075132 | A1* | 3/2010 | Waid et al. ................ 428/317.3 | WO | WO 01/87589 | 11/2001 |
| | | | | WO | WO 02/083786 | 10/2002 |
| | | | | WO | WO 03/047488 | 6/2003 |
| | | | | WO | WO 03/082571 | 10/2003 |
| | | | | WO | WO 2006/074481 | 7/2006 |

FOREIGN PATENT DOCUMENTS

| | | |
|---|---|---|
| DE | 1910911 | 3/1969 |
| EP | 0119827 | 7/1988 |
| EP | 0316671 | 11/1988 |
| EP | 0433951 | 6/1991 |
| EP | 0 591 647 A | 4/1994 |
| EP | 0 597 331 A | 5/1994 |
| EP | 0451919 | 2/1995 |
| EP | 0650714 | 5/1995 |
| EP | 0 703 068 A | 3/1996 |
| EP | 0847738 | 6/1998 |
| EP | 1351815 | 2/2005 |
| EP | 1013291 | 6/2005 |
| EP | 1226018 | 10/2005 |
| GB | 2297473 | 8/1995 |
| GB | 2287888 | 10/1995 |
| GB | 2328158 | 2/1999 |
| GB | 2329842 | 4/1999 |
| JP | 62241944 | 10/1987 |
| JP | 63238153 | 10/1988 |
| JP | 3160083 | 7/1991 |
| JP | 3160084 | 7/1991 |
| JP | 3239738 | 10/1991 |
| JP | 4153288 | 5/1992 |
| JP | 7157738 | 6/1995 |
| JP | 8060120 | 3/1996 |
| JP | 8060121 | 3/1996 |
| JP | 8277382 | 10/1996 |

OTHER PUBLICATIONS

J.H. Briston, *Plastic Films*, 2$^{nd}$ Edition, Longman Inc., New York (1983), pp. 83-85.

I.M. Ward, *Mechanical Properties of Solid Polymers*, Wiley-Interscience, New York (1971), p. 278.

U.S. Appl. No. 11/144,508, filed Jun. 3, 2005, Herd et al., Office Action dated Mar. 16, 2009.

U.S. Appl. No. 11/144,508, filed Jun. 3, 2005, Herd et al., Office Action dated Jul. 16, 2008.

U.S. Appl. No. 11/144,508, filed Jun. 3, 2005, Herd et al., Office Action dated May 18, 2007.

U.S. Appl. No. 11/145,353, filed Jun. 3, 2005, McKiernan et al., Office Action dated Feb. 10, 2009.

U.S. Appl. No. 11/145,353, filed Jun. 3, 2005, McKiernan et al., Office Action dated Jul. 30, 2008.

U.S. Appl. No. 11/145,353, filed Jun. 3, 2005, McKiernan et al., Office Action dated Dec. 11, 2007.

U.S. Appl. No. 11/144,497, filed Jun. 3, 2005, McKiernan et al., Office Action dated Jan. 22, 2009.

U.S. Appl. No. 11/144,497, filed Jun. 3, 2005, McKiernan et al., Office Action dated May 1, 2008.

* cited by examiner

DISPOSABLE PULL-ON DIAPER HAVING A LOW FORCE, SLOW RECOVERY ELASTIC WAIST

CROSS REFERENCE TO RELATED APPLICATIONS

This application claims the benefit of U.S. Provisional Application No. 60/647,246, filed Jan. 26, 2005.

FIELD OF THE INVENTION

The present invention relates to an absorbent article having an elastic belt that exhibits slow recovery elongation. The present invention relates to an absorbent article having an elastic belt that exhibits a gradual increase in force upon recovery.

BACKGROUND OF THE INVENTION

It has long been known that absorbent articles such as conventional taped diapers, pull-on diapers, training pants, sanitary napkins, pantiliners, incontinence briefs, and the like, offer the benefit of receiving and containing urine and/or other bodily exudates. To effectively contain exudates, the articles should provide a snug fit around the waist and legs of a wearer. Articles such as conventional diapers generally include a front and a rear waist section releasably connected by a fastening means. Application of a conventional diaper is usually performed by a caregiver with the wearer in a supine position. Such diapers may allow for easy application by the caregiver but generally make self-application by the wearer very difficult. Furthermore, conventional diapers may be difficult to apply when the wearer is in a standing position.

Disposable pull-on diapers were developed, in part, to address the problem associated with conventional diapers such as difficulties related to self-application and standing application. Pull-on diapers are designed to effectively contain exudates while allowing for self-application. Pull-on diapers generally include a front waist region, a back waist region, and a crotch region therebetween. The front waist region and back waist region may be attached to form a waist opening and pair of leg openings. Generally, pull-on diapers are manufactured in a prejoined configuration such that the front and rear waist sections do not need to be attached by a wearer or caregiver prior to wear. In one particular facet, pull-on diapers have become popular for use on children who are able to walk and who may be engaged in toilet training. Pull-on diapers may serve as an intermediary product for the child between a conventional diaper and underwear. The pull-on provides a milestone for the child who may be toilet training and developing independence from the caregiver. However, to be an effective advance over a conventional diaper, the pull-on should not only allow for self-application but should also provide a mechanism for easier self-application.

Unfortunately, current pull-on diapers may be difficult for self-application by a child. Many pull-on diapers have elastic elements in the portion of the pull-on diaper that encircles the waist of the child during wear. The elastic elements allow the pull-on diaper to achieve a snug, conforming fit about the waist of the child. The elastic elements also allow the pull-on diaper to fit a range of shapes and sizes thereby enabling the pull-on diaper to exhibit a degree of customized fit. While the elastic elements are beneficial once applied, the elastic elements may inhibit the process of application and, particularly, self-application. During application, the waist opening of a pull-on diaper may be enlarged from its relaxed dimensions. Enlargement of the waist opening is often necessary given the geometry of a child wearer. As the pull-on diaper is pulled from a child's feet to the child's buttocks, the circumference of the child generally increases. Ideally, the pull-on diaper will maintain an enlarged waist opening during the application process. Specifically, throughout the application process, the waist opening circumference should stay larger than the circumference of the child over which the waist opening must pass. Child studies have shown that self-application of a garment (e.g., underwear or pull-on diaper) may take anywhere from about 12 seconds to about 2 minutes depending upon factors such as the child's size, dexterity, strength, and attention span. Typically, self-application may take from about 15 seconds to about 30 seconds.

However, existing pull-on diapers do not maintain an enlarged waist opening once elongated. Elastic elements within the pull-on diaper may exert a force that constricts the waist opening. The child or caregiver may need to exert a lateral force either to increase the size of the waist opening of the pull-on diaper or to maintain the size of the waist opening. The need to exert a lateral force may exist if the waist opening of the pull-on diaper constricts to a circumference smaller than a circumference of the child over which the diaper must pass at some given time of application. For example, the region of the buttocks typically is the greatest circumference over which pull-on diaper must pass. A lateral force may need to be applied to the pull-on diaper if the diaper's waist opening is smaller than the circumference around the child's buttocks when the diaper passes over the buttocks during application.

It should also be appreciated that any constrictive force pressing against the body of the wearer results in friction that must be overcome in the application process. If the pull-on diaper is in contact with wearer's body as the diaper is applied, the waist opening must continue to expand which results in increased strain upon the elastic elements. Increased strain often results in increased normal forces which further increases the friction that must be overcome by the child. Given a child's limited dexterity and strength, an increase in friction may make successful application of the pull-on diaper impossible.

Furthermore, as the pull-on diaper is advanced up the legs, the anatomy of the wearer may serve as a geometric barrier to application. The buttocks may serve as barrier that can catch the waist edge of the pull-on diaper and effectively prevent further upward advancement of the pull-on diaper. The waist opening may need to be enlarged to a circumference generally greater than that of the buttocks. The forces exhibited by elastic elements in current products may make enlargement of the waist circumference difficult for the applicator and impossible for a child.

Another factor making application of a pull-on diaper difficult is waist opening deformation. Ideally, the shape of waist opening of the pull-on diaper should mirror the shape of the wearer and, particularly the shape of the child at the point of greatest circumference. Generally, a circular or elliptical (e.g., an ellipse having an aspect ratio of approximately 1:1 to 1:2) shaped waist opening are preferred. However, if the waist opening must be enlarged, this preferred waist opening shape can be deformed. For example, in enlarging the waist opening, the applicator typically grasps the pull-on diaper at two points evenly spaced around the waist edge. Applying a lateral force creates a line of force traveling between the grasp points. As the waist opening elongates along this line of force, the waist opening may draw in or neck in a direction perpendicular to the lateral line of force. Since the applicator often grasps the sides of the pull-on diaper that are proximate to the hips of the wearer, the pull-on diaper may neck between the front and the back of the diaper. Necking of the diaper in the front and the back may further hinder application since the waist opening is being necked in at the point where the wearer's geometry protrudes, the buttocks.

Even if a caregiver wishes to aid the wearer in self-application, current pull-on diapers may frustrate such efforts. A caregiver may enlarge the size of the waist opening of a pull-on diaper before providing the pull-on diaper to the wearer for application. Ideally, the caregiver may stretch the waist opening to a circumference greater than that of the lower torso of the wearer. However, if the elongating force is not maintained, the pull-on diaper will typically "snap back" to substantially its original, relaxed dimension due to the force exerted by the elongated elastic elements. The elastic elements of current pull-on diaper construction are aggressive in that they contract rapidly and exert relatively high forces. As a result, if the pull-on diaper is expanded by a caregiver and then provided to a child, the child is left with a pull-on diaper that may require application of a continuous elongating force or else the product returns to its original, relaxed dimension.

In light of the problems described above, it is desirable to provide a disposable pull-on diaper that is tailored for ease of application and, especially, ease of self-application by a child. It would be beneficial to provide a disposable pull-on diaper having a waist circumference that retains its elongated state for some period of time after release of the elongating force. It would be particularly beneficial if this period of time approximates the average time necessary for the application process. It would also be beneficial to provide a disposable pull-on diaper requiring only minimal force to maintain elongation or to re-elongate the pull-on diaper. It would also be beneficial if the pull-on diaper exerted a gradual increase in force upon recovery.

DETAILED DESCRIPTION OF THE INVENTION

Figure 1A:
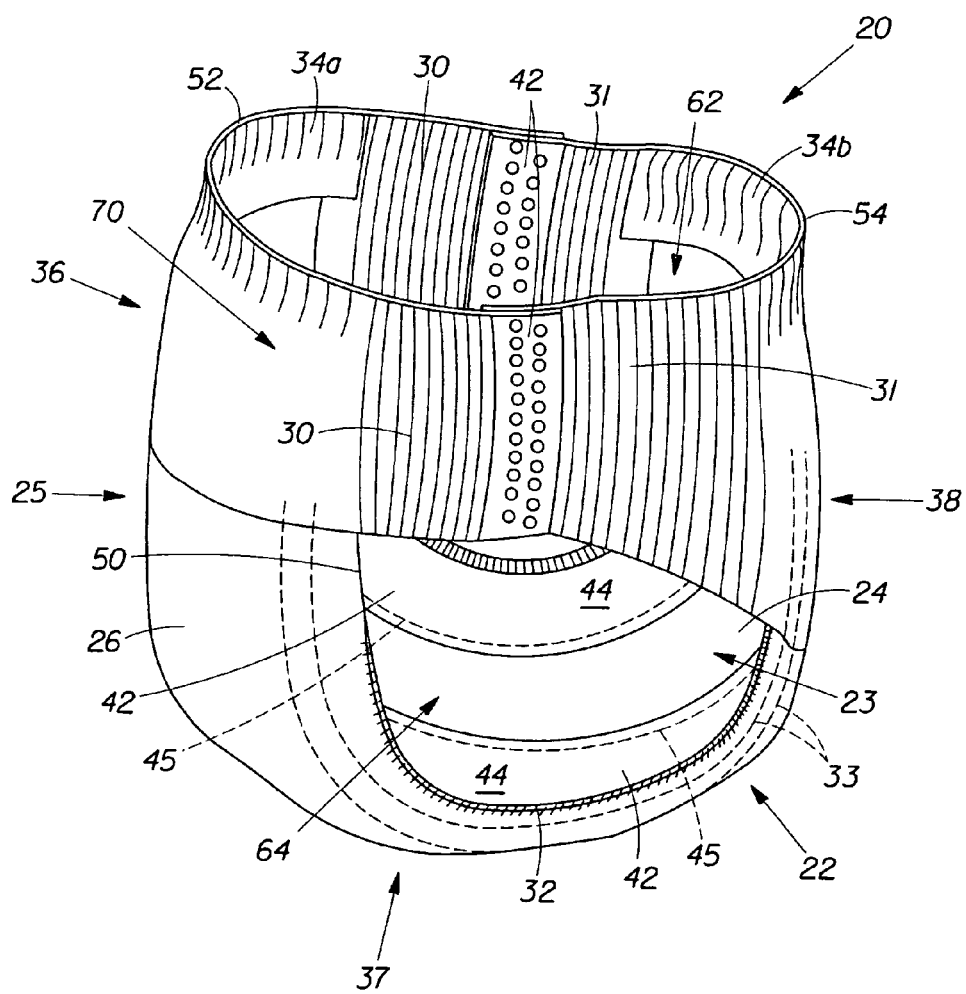
FIG. 1a is a perspective view of a disposable pull-on diaper according to the present invention.

The term "absorbent article" herein refers to a device which absorbs and contains excreta and/or bodily exudates and, more specifically, refers to a device which is placed against or in proximity to the body of the wearer to absorb and contain the excreta and/or exudates discharged from the body. The term "unitary absorbent article" herein refers to an absorbent article which is formed of separate parts united together to form a coordinated entity so that separate manipulative parts, such as a separate holder and/or liner, are not required. The term "disposable article" herein refers to an article which generally is not intended to be restored or reused, but is instead intended to be discarded after a single use. The term "diaper" refers to an absorbent article generally worn by infants and incontinent persons about the lower torso. The present invention is applicable to absorbent articles such as diapers, pull-on diapers or pant-type garments, training pants, incontinence briefs, incontinence undergarments, absorbent inserts, diaper holders and liners, feminine hygiene garments, and the like.

The term "joined" refers herein to the attachment together of elements of the absorbent article, either by direct affixment of a first element to a second element or by affixment of the first element to an intermediate element which is affixed to the second element.

As used herein, the term "longitudinal" generally refers to a line, axis, or direction which lies within the plane of the absorbent article or pull-on garment that is generally aligned with (e.g., approximately parallel including directions within +45° of the longitudinal direction) a longitudinal centerline.

As used herein, the terms "lateral" or "transverse" refer to a line, axis or direction which lies within the plane of the absorbent article or pull-on garment that is generally perpendicular to the longitudinal centerline.

The terms "elastic" and "elastically extensible" refer herein to the property of a material and/or an element of a diaper whereby the material and/or the element can be elongated to a practical extent upon the application of tensioning force and will substantially return to its original length or near its original length after the tension is released.

The term "elastic belt" refers herein to a portion of an absorbent article that encircles the waist of a wearer and exhibits some degree of elasticity. The elastic belt may be generally contiguous with the front and back waist regions. The elastic belt may comprise one or more elements that contribute to a circumferential tension about the waist opening of a diaper; such elements may be continuous or discontinuous. Generally, the tension is exhibited during expansion of the waist opening for application and/or exhibited when the diaper is worn.

The term "aged" as used herein with reference to a material and, particularly, to an elastomeric composition means that the material or elastomer was manufactured at least about 6 months, 12 months, 18 months, or 24 months, prior to incorporation into an absorbent article.

The term "pre-closed" refers herein to an absorbent article in which the article is assembled and ready for use. Typically, "ready for use" means that a waist opening and a pair of leg openings are present in the article and do not need to be formed by user intervention such as by applying a fastening member or engaging a fastening system.

The present invention relates generally to an absorbent article, especially a pull-on diaper, having an elastic belt that can be elongated, that maintains some degree of the elongation during the process of application of the article, and that elastically recovers to provide an elastic fit force during wear. For purposes of this invention, the ability of an elastic belt of the diaper to be elongated, to maintain elongation, and to elastically recover is quantified by reference to a Percent Release Test Method, as provided below. In certain embodiments, the elastic belt will exhibit a Percent Maximum Force at 15 seconds exhibited by the elastic belt will be less than about 80%-20% of the maximum force as measured by the Percent Release Test. In certain embodiments, the elastic belt will exhibit a Percent Maximum Force at 45 seconds exhibited by the elastic belt will be less than about 90%-55% of the maximum force as measured by the Percent Release Test.

In certain embodiments, the elastic belt may exhibit a 30% Recovery Time of at least 0.1 second. In certain embodiments, the elastic belt may exhibit a 30% Recovery Time of at least 1 second. In certain embodiments, the elastic belt may exhibit a 30% Recovery Time of at least 5 seconds. In certain embodiments, the elastic belt may exhibit a 30% Recovery Time of at least 10 seconds. In particular embodiments, the absorbent article may remain elongated for at least enough time so that the article can be applied to the wearer.

In certain embodiments, the elastic belt may exhibit a recovery speed of less than about 508 mm/min. In other embodiments, the elastic belt may exhibit a maximum normalized force of at least about 0.15 N/cm as measured by the Percent Release Test.

In certain embodiments, the elastic belt may exhibit a Percent Release of at least 30-90% after 180 seconds as measured by the Percent Release Test.

In particular embodiments, the force to achieve elongation of the waist opening may be no greater than certain prescribed values. Likewise, in certain embodiments, it is desirable that the article exhibit a force about the waist of the wearer while in normal use. As a result, the article may exhibit at least a prescribed elastic force upon recovery and during wear.

Figure 1B:
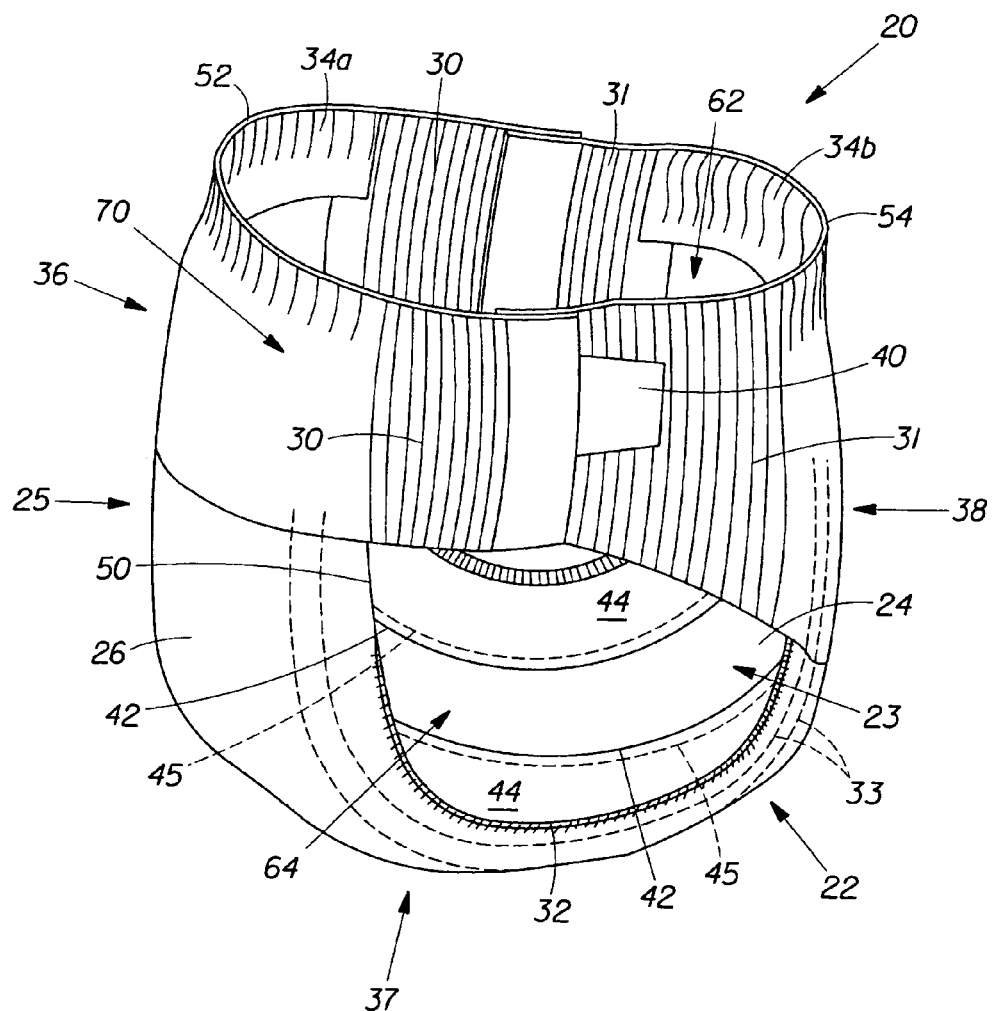
FIG. 1b is a perspective view of a disposable pull-on diaper according to the present invention showing a fastening system.

An exemplary embodiment of an absorbent article of the present invention is the unitary disposable absorbent article in a pant form, pull-on diaper 20, shown in FIGS. 1a-b. The diaper 20 of FIG. 1a is shown in a flat and uncontracted state in FIG. 2 with the portion of the diaper 20 which faces the wearer (i.e., body-facing surface) oriented toward the viewer. Elements of the diaper 20 which are substantially identical in different embodiments and/or in different drawings are designated herein by the same numerals.

The diaper 20 may include an absorbent assembly 22, waist features 34a, 34b, and side panels 30, 31. The diaper 20 has a front waist region 36, a back waist region 38 opposed to the front waist region 36, and a crotch region 37 located between the front waist region 36 and the back waist region 38. The periphery of the diaper 20 is defined by the outer edges of the diaper 20 in which side edges 50 lie generally parallel to the longitudinal centerline 100 and the front waist edge 52 and back waist edge 54 lie generally parallel to the lateral centerline 110 of the diaper 20 and extend between the side edges 50.

The absorbent assembly 22 of the diaper 20 may include a liquid pervious topsheet 24, a liquid impervious backsheet 26, and an absorbent core 28 which may be positioned between at least a portion of the topsheet 24 and the backsheet 26. The absorbent assembly 22 may constitute the main structure of the diaper with other features added to form the composite diaper structure. The absorbent assembly 22 and generally all elements of diaper 20 may have a body-facing surface 23 which generally is in contact with the body or in close proximity to the body when the article is worn. The absorbent assembly 22 may have a garment-facing surface 25 opposed to the body-facing surface 23 and which generally contacts with or may be in close proximity to any garment being worn. The topsheet 24, the backsheet 26, and the absorbent core 28 may be assembled in a variety of configurations well known in the art. Exemplary absorbent assembly structures are described in U.S. Pat. No. 5,899,895 issued May 4, 1999 and U.S. Pat. No. 6,120,487 issued Sep. 19, 2000.

The backsheet 26 is generally that portion of the diaper 20 which is disposed adjacent the garment-facing surface of the absorbent core 28 and which prevents the excreta and/or exudates contained therein from soiling garments or other articles which may contact the diaper 20, such as bedsheets and clothing. In preferred embodiments, the backsheet 26 may be substantially impervious to liquid and may comprise any suitable thin plastic film known in the art, including a breathable film. Exemplary backsheet films include those manufactured by Tredegar Industries, Inc., or Terre Haute, Ind., USA, and sold under the trade names X15306, X10962, and X10964.

The backsheet 26 may be joined to the topsheet 24, the absorbent core 28 or any other element of the diaper 20 or absorbent assembly 22 by any attachment means known in the art. For example, the attachment means may include a uniform continuous layer of adhesive, a patterned layer of adhesive, or an array of separate lines, spirals, or spots of adhesive. Exemplary adhesives include those manufactured by H.B. Fuller Company of St. Paul, Minn., USA and marketed as HL-1620 and HL-1358-XZP. Alternatively, the attachment means may comprise heat bonds, pressure bonds, ultrasonic bonds, dynamic mechanical bonds, or any other suitable attachment means or combinations of attachment means known in the art.

The topsheet 24 is preferably disposed adjacent the body-facing surface of the absorbent core 28 and may be joined to the absorbent core 28 and/or to the backsheet 26 by any attachment means known in the art. The topsheet 24 is preferably compliant, soft-feeling, and non-irritating to the wearer's skin. Preferably, at least a portion of the topsheet 24 is liquid pervious, permitting liquids to readily penetrate through its thickness. A suitable topsheet may be manufactured from a wide range of materials known in the art, such as porous foams, reticulated foams, apertured plastic films, or woven or nonwoven materials of natural fibers such as wood or cotton fibers, or synthetic fibers such as polyester or polypropylene fibers, or a combination of natural and synthetic fibers. If the topsheet 24 includes fibers, the fibers may be spunbond, carded, wet-laid, meltblown, hydroentangled, or otherwise processed as is known in the art. One suitable topsheet material is a thermobonded carded web which is available as Supplier Code No. P-8 from Fiberweb North America, Inc., Simpsonville, S.C., U.S.A.

The absorbent core 28 may comprise any absorbent material which is generally compressible, conformable, non-irritating to the wearer's skin, and capable of absorbing and retaining liquids such as urine and other bodily exudates. The absorbent core 28 may be manufactured in a wide variety of sizes and shapes, for example, rectangular, hourglass, "T"-shaped, asymmetric, etc. The absorbent core 28 may include any of a wide variety of liquid-absorbent materials commonly used in disposable diapers and other absorbent articles, such as comminuted wood pulp, which is generally referred to as airfelt, cellulose wadding, meltblown polymers, chemically stiffened, modified, or cross-linked cellulosic fibers, tissue, absorbent foams including those prepared from polymerization of a high internal phase emulsion, superabsorbent polymers, absorbent gelling materials, or any other known absorbent material or combinations of materials. Exemplary absorbent core structures are described in U.S. Pat. No. 4,610, 678 issued Sep. 9, 1986 and U.S. Pat. No. 5,260,345 issued Nov. 9, 1993.

Figure 2:
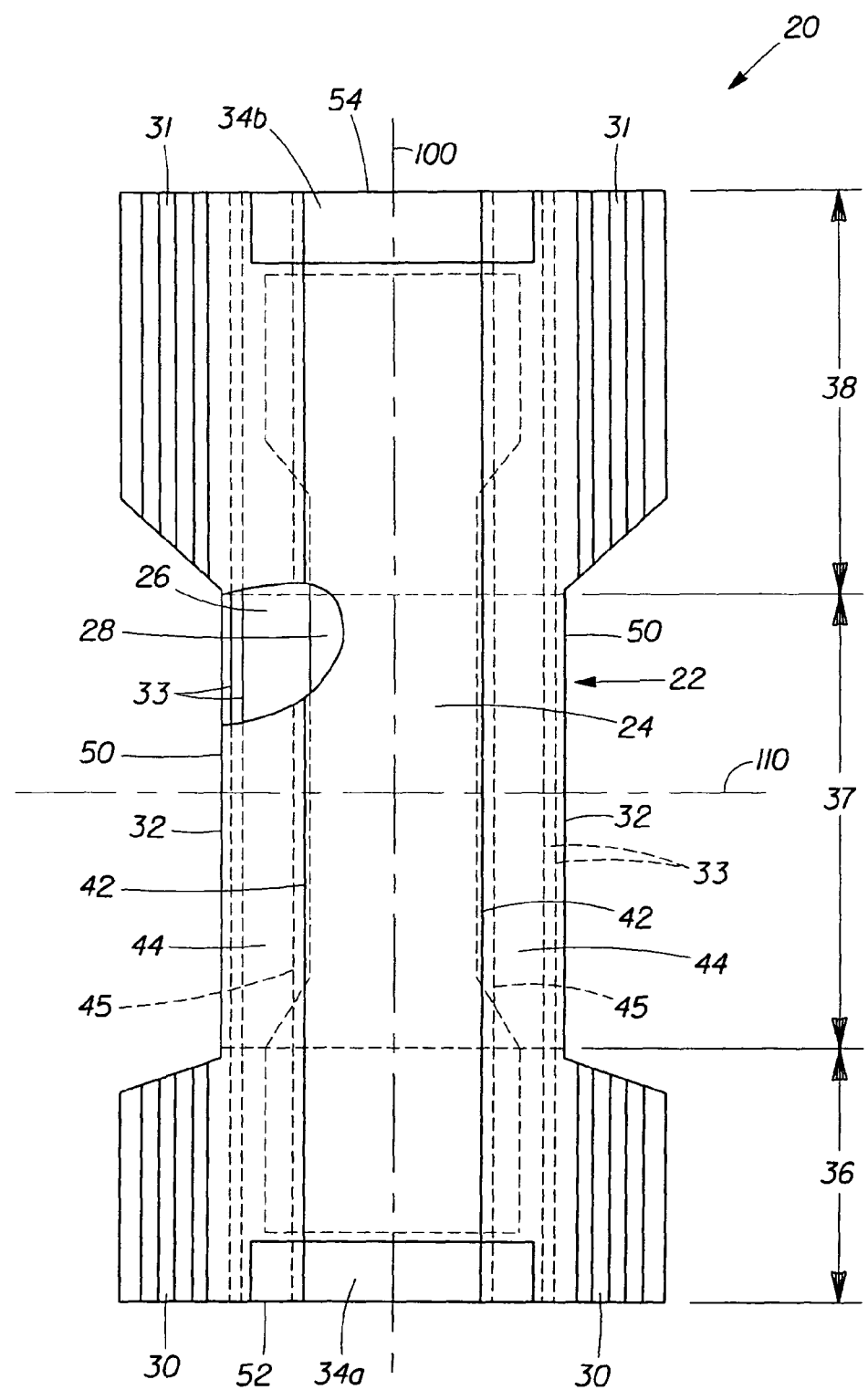
FIG. 2 is a perspective view of the disposable pull-on diaper of FIG. 1 laid flat in its unseamed, uncontracted state.

Diaper 20 may include at least one leg cuff. FIGS. 1-2 show diaper 20 with two pairs of leg cuffs: gasketing cuffs 32 and barrier cuffs 42. Leg cuffs are known variously in the art as gasketing cuffs, containment flaps, "stand-up" elasticized flaps, barrier cuffs, leg bands, side flaps, and/or elastic cuffs. The leg cuffs may be constructed in any suitable configuration known in the art, including those described in U.S. Pat. No. 4,695,278 issued Sep. 22, 1987, and U.S. Pat. No. 4,795, 454 issued Jan. 3, 1989.

The barrier cuff 42 may be formed by a flap 44 and an elastic member 45. The flap 44 may be a continuous extension of any of the existing materials or elements that forms diaper 20. For example, flap 44 may be a portion of the topsheet 24 treated to be hydrophobic or the flap 44 may be a discrete element separately attached to diaper 20. The elastic member 45 may be an elastic material that provides elasticity to the barrier cuff 42. It is desirable that elastic member 45 exhibits sufficient elasticity such that the barrier cuff may remain in contact with the wearer during normal wear thus enhancing the barrier properties of the barrier cuff 42. U.S. Pat. Nos. 4,808,178 and 4,909,803 describe disposable diapers having barrier cuffs that improve the containment at the leg regions.

The gasketing cuff 32 may be substantially inelastic or may be elastically extensible to dynamically fit at the wearer's leg. The gasketing cuff 32 may be formed by one or more elastic members 33 operatively joined to the topsheet 24, backsheet 26, flap 44, or any other substrate used in the formation of diaper 20. In one suitable embodiment, the gasketing cuff 32 has a plurality of elastic members 33 joined between the backsheet 26 and the flap 44. U.S. Pat. No. 3,860,003 describes a disposable diaper which provides a contractible leg opening having a side flap and one or more elastic members to provide an elasticized leg cuff.

In some embodiments, such as that shown in FIG. 1b, the diaper 20 may include a fastening system 40. The fastening system 40 preferably maintains the front waist region 36 and the back waist region 38 in a hoop configuration such that lateral force exerted by an elastic belt contributes to a circumferential tension when the diaper 20 is worn. The vector of the circumferential tension may be aligned substantially parallel to the front waist edge 52 and back waist edge 54, which form the waist opening 21. The fastening system may be disposed anywhere provided that the fastening system maintains the circumferential elastic belt during wear. The fastening system 40 may be disposed at least partially adjacent at least a portion of the side edges 50 of the front waist region 36 and/or the back waist region 38. In general, the fastening system 40 may comprise any known fastening means. For example, the fastening system 40 may comprise surface fasteners such as tape tabs, hook and loop fastening components, and/or hermaphroditic fastening components. Furthermore, the fastening system 40 may include buttons, hooks, buckles, and/or other fastening components. In some embodiments, the fastening system 40 may include refastenable fastening means that allow the diaper 20 to be opened and re-fastened, for ease of fitting on and removal from the body of the wearer and for adjustment while the diaper 20 is worn. In certain embodiments, the fastening system 40 may comprise an engaging member and a receiving member. Suitable combinations of engaging members and receiving members include, respectively, hook to loop; adhesive to substrate; selective adhesive to substrate; cohesive to cohesive; variant thereof; and combinations thereof. A suitable fastening system 40 is described in U.S. Pat. No. 5,242,436 issued Sep. 7, 1993.

In some embodiments, the diaper 20 may be provided in a pre-closed form as shown, for example, in FIGS. 1a-b. The pre-closed diaper 20 may have its opposing side edges 50 in the front waist region 36 and the back waist region 38 joined by seams 42. The seams 42 may be formed by any suitable bonding means known in the art which is appropriate for the specific materials employed. For example, suitable bonding means may include ultrasonic sealing, heat sealing, pressure bonding, adhesive bonding, sewing, autogenous bonding, and the like. The seams 42 may be permanent, that is, they may be bonded such that separation of the joined opposing side edges 50 requires the rupture or other destructive manipulation of the bonded materials that prevents refastening of the side edges 50.

The diaper 20 may alternatively have its opposing side edges 50 fastened together by any suitable fastening means, including those described above for the fastening system 40 as shown in FIG. 1b. In some embodiments, the fastening system 40 of a pre-closed diaper 20 may be refastenable such that diaper 20 can be opened and re-fastened. A refastenable fastener may provide for easier application, removal, and adjustment. In one embodiment of a pre-closed diaper 20 having a fastening system 40 as shown in FIG. 1b, the fastening system 40 may be disposed at least partially adjacent at least a portion of the side edges 50 of the front waist region 36 and/or the back waist region 38.

The diaper 20 of the present invention may include an elastic belt 70 such that, when diaper 20 is in a closed configuration, the front waist region 36 and the back waist region 38 are joined to yield a continuous waist edge comprising a front waist edge 52 and a back waist edge 54 which together define a waist opening 62 and two leg openings 64. The elastic belt 70 may be constructed from one or more elastic elements such that, in a closed configuration, a lateral force exerted by said elastic element contributes to a circumferential tension when the diaper 20 is extended or stretched for application or when the diaper 20 is worn. The elastic belt 70 may be formed by a variety of elements or combination of elements.

One suitable element that may be used to form the elastic belt 70 is a waist feature 34a, 34b. The waist feature 34a, 34b may be disposed longitudinally outwardly from at least one of the waist edges 56 of the absorbent core 28. The waist feature 34a, 34b may be disposed along the front waist edge 52 and/or the back waist edge 54 of the diaper 20; generally the waist feature 34a, 34b will form a portion of the front waist edge 52 and/or the back waist edge 54. The waist feature 34a, 34b may comprise one or more separate elements affixed to the diaper 20 and/or may comprise a continuous extension of another element or substrate of the diaper 20, such as the backsheet 26 and/or the topsheet 24. For example, as illustrated in FIGS. 1a-b, diaper 20 may have a front waist feature 34a and a back waist feature 34b that are discontinuous in relation to one another. Alternatively, the front waist feature 34a and the back waist feature 34b may overlap or be positioned proximate to one another so as to effectively perform as a single waist feature. Alternatively, the waist feature 34a, 34b may span a portion of both the front waist region 36 and the back waist region 38. It may be desirable for the waist feature to completely span the front waist region 36 and the back waist region 38 so as to provide 360° elasticity to the elastic belt.

The waist feature 34a, 34b may be at least laterally elastically extensible to provide circumferential tension at the diaper waist opening 62. The waist feature 34a, 34b may be constructed in any of several different configurations known in the art. In one embodiment, waist feature 34a, 34b may be a stretch laminate comprising one or more substrates with elastic members joined thereon or therebetween. An exemplary waist feature 34a, 34b may be a stretch laminate comprising two layers of nonwoven material with a plurality of elastic strands stretch bonded therebetween. Such a waist feature 34a, 34b may be formed discretely and then joined to the diaper 20 or the waist feature may be formed unitarily within the diaper. As an example of a unitary formation, the waist feature 34a, 34b may comprise a plurality of elastic strands stretch bonded between two existing layers or substrates of the diaper (e.g., between the topsheet and the backsheet). Other exemplary waist feature constructions include those described in U.S. Pat. No. 4,515,595 issued May 7, 1985 and U.S. Pat. No. 5,221,274 issued Jun. 22, 1993.

One suitable element that may be used to form the elastic belt 70 is one or more side panels 30, 31. The diaper 20 may also include side panels 30, 31 disposed in the in the front waist region 36 and the back waist region 38, respectively. The side panels 30, 31 may be constructed in any suitable configuration known in the art. The side panels 30, 31 may be elastically extensible. A suitable elastic side panel is described in U.S. Pat. No. 5,669,897 issued Sep. 23, 1997.

The side panels 30, 31 may be integral with the absorbent assembly 22 (i.e., they may be continuous extensions of one or more of the layers of the absorbent assembly 22) or they may be separately attached to the main absorbent assembly 22. Alternatively, the side panels 30, 31 may be made of multiple components or layers some of which are discrete (i.e., either attached separately to the main absorbent portion or separated therefrom by a gap) and some of which are continuous. An example of this type of construction is a diaper provided with an outer nonwoven cover which completely covers all areas of the diaper 20 including the side panels 30, 31 and the absorbent assembly 22.

The side panels 30, 31 together with the absorbent assembly may form pull-on diaper 20 having a waist opening and a pair of leg openings, when said pull-on diaper is in a closed configuration. As shown in FIGS. 1-2, the diaper 20 has a pair of front side panels 30 disposed generally transversely outward from the longitudinal edges of the absorbent assembly and at or near the front waist region 36. Similarly, the diaper 20 has a pair of rear side panels 31 disposed generally transversely outward from the longitudinal edges of the absorbent assembly and at or near the rear waist region 38. The respective waist regions 36, 38 together with the side panels 30, 31 may form a continuous waist opening when the side panels 30, 31 are joined such by the seam 42 in FIG. 1a or by the fastening system 40 in FIG. 1b. Similarly, the main absorbent assembly 22 and the side panels 30 also form leg openings.

The front side panels 30 and the rear side panels 31 may be joined by a bonding method to form a seam 42. The front side panels 30 and the rear side panels 31 may be bonded by any suitable bonding means known in the art which is appropriate for the specific materials employed. For example, suitable bonding methods may include ultrasonic sealing, heat sealing, pressure bonding, adhesive bonding, sewing, autogenous bonding, and the like. The seams 42 may be permanent in that separation of the joined side panels 30, 31 requires the rupture or other destructive manipulation of the side panels 30, 31 effectively preventing refastening of the side panels 30, 31.

As shown in FIGS. 1a-b, front side panel 30 and rear side panels 31 may be joined at a point such that each side panel 30, 31 had approximately the same lateral width. However, the side panels 30, 31 may be joined at various locations. Furthermore, while FIGS. 1a-b show a front side panel 30 and a rear side panel 31 being joined to form the waist opening 62 and a pair of leg openings 64, a single front or rear side panel may join the front waist region to the rear waist region thereby forming the waist opening and pair of leg openings.

In certain embodiments, it is desirable that the side panels 30, 31 be extensible and/or elastic. The side panels 30, 31 may be made extensible or elastic by any of a variety of techniques known in the art. For example, an elastic side panel 30, 31 can be made by disposing an elastic member, such as elastic strands or films, between facing layers of cover material, such as a non-woven material. Typically, in such a construction the elastic stands are attached to the facing layers while in a stretched configuration. After attachment, the strands are allowed to relax thereby gathering the facing layers and creating an elastic laminate. In an alternative method, elastic strands or a film can be attached to one or more facing layers in either a relaxed configuration or partially stretched configuration. The resulting laminate can be made stretchable (or more stretchable in the case of partially stretched strands or film) by subjecting the laminate to an elongation process which elongates the facing layers permanently, but the elastic stands or layer only temporarily. Such processes are known in the art as "zero strain" stretch laminate formation, and the elongation of such laminates may be accomplished with suitable means such as rollers, engaging teeth, or the like. Examples of zero strain activation processing and formations of resulting stretchable laminates are described in U.S. Pat. No. 5,167,897 issued to Weber et al. and U.S. Pat. No. 5,156,793 issued to Buell et al.

In certain embodiments, the elastic belt may be constructed from a combination of elements. For example, in FIGS. 1-2, the diaper 20 is shown with side panels and waist features.

Figure 3:
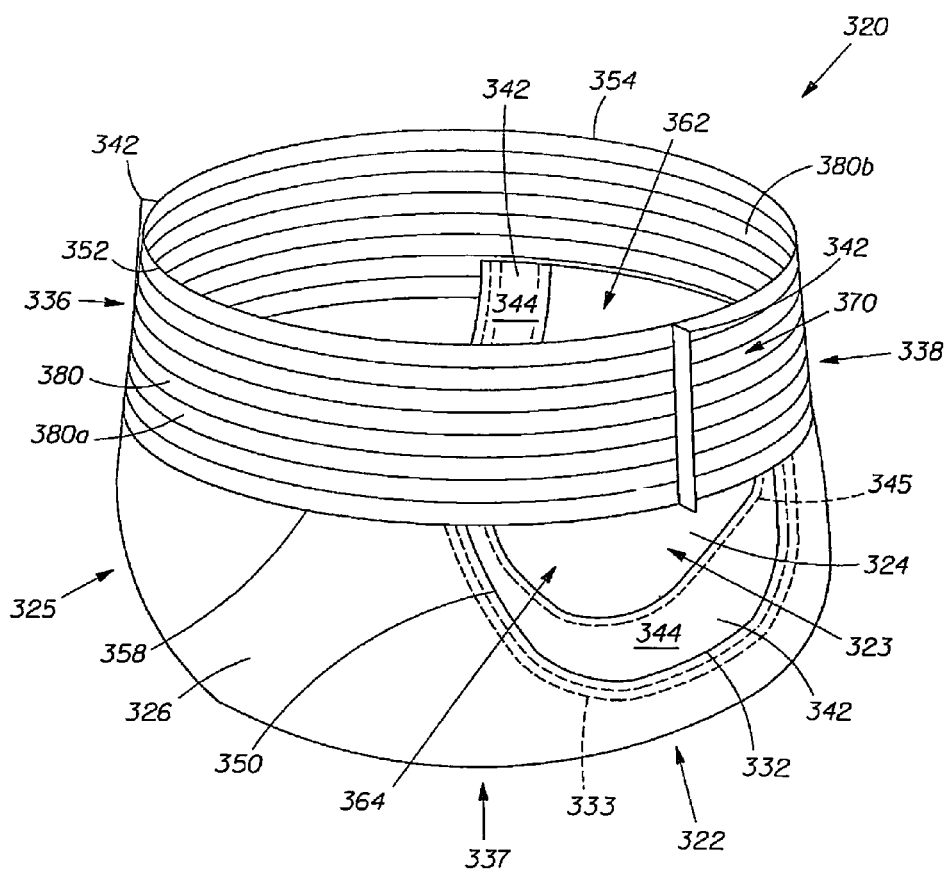
FIG. 3 is a perspective view of a disposable pull-on diaper according to the present invention.
Figure 4:
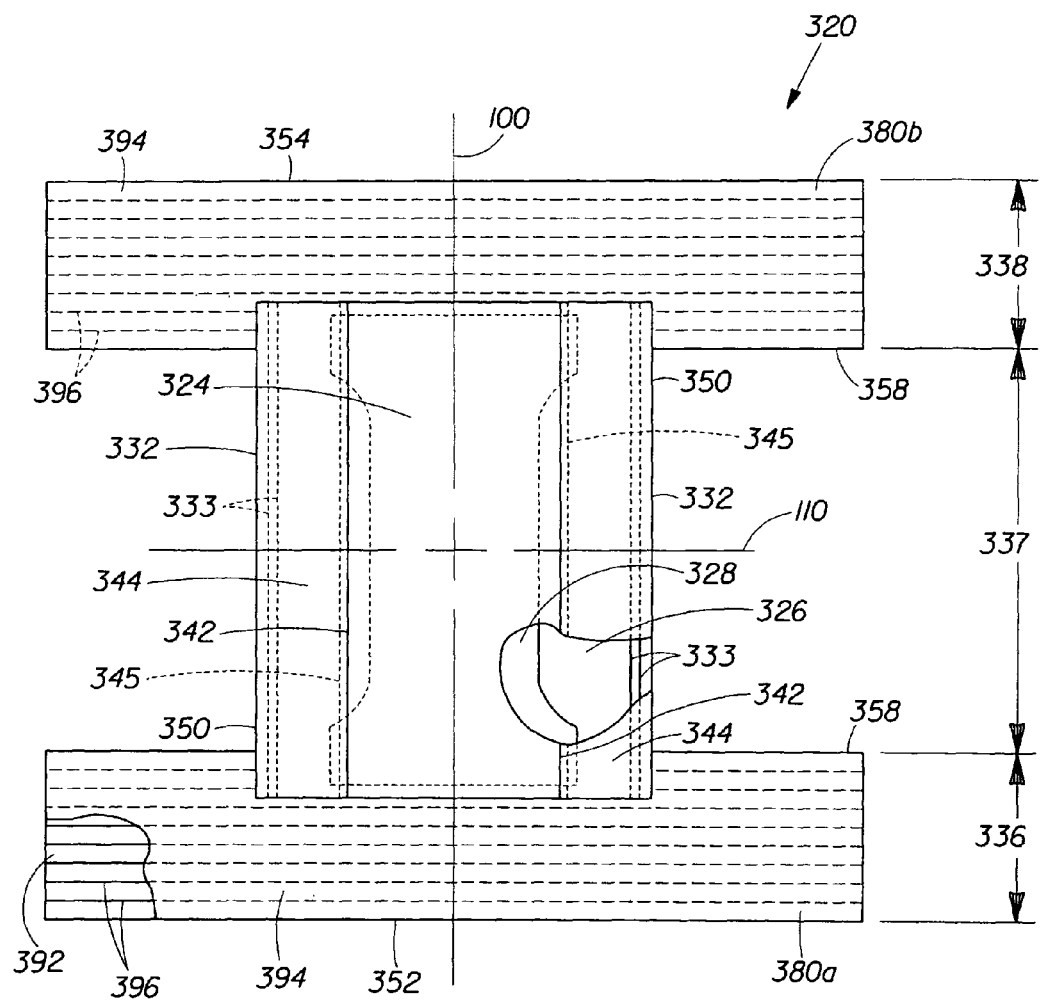
FIG. 4 is a perspective view of the disposable pull-on diaper FIG. 3 laid flat in its unseamed, uncontracted state.

FIGS. 3 and 4 illustrates another embodiment of a pull-on diaper 320. FIG. 3 is a perspective view of diaper 320 having an absorbent assembly 322 and an elastic belt 370 in the form of a unitary waistband 380. The diaper 320 in open, unseamed form is shown in FIG. 4. Unless specifically stated otherwise, elements of the diaper 320 are substantially identical in composition and formation to the like elements in the embodiments provided above and shown in FIGS. 1-2.

The diaper 320 has a front waist region 336, a back waist region 338 opposed to the front waist region 336, and a crotch region 337 located between the front waist region 336 and the back waist region 38. The periphery of the diaper 320 is defined by the outer edges of the diaper 320 in which side edges 350 lie generally parallel to the longitudinal centerline 100 and the front waist edge 352 and back waist edge 354 lie generally parallel to the lateral centerline 110 of the diaper 320 and extend between the side edges 350.

The absorbent assembly 322 of the diaper 320 may include a liquid pervious topsheet 324, a liquid impervious backsheet 326, and an absorbent core 328 which may be positioned between at least a portion of the topsheet 324 and the backsheet 326. The absorbent assembly 322 may have an inner body-facing surface 323 which generally is in contact with the body or in close proximity to the body when the article is worn. The absorbent assembly 322 may also have an outer garment-facing surface 325 opposed to the inner surface 323 and which generally contacts with or may be in close proximity to any garment being worn. The topsheet 324, the backsheet 326, and the absorbent core 328 may be assembled in a variety of configurations well known in the art. Exemplary absorbent assembly structures are described in U.S. Pat. No. 5,899,895 issued May 4, 1999 and U.S. Pat. No. 6,120,487 issued Sep. 19, 2000.

Diaper 320 may include at least one leg cuff; FIGS. 3-4 show diaper 320 with two pairs of leg cuffs; gasketing cuff 332 and barrier cuff 342. Leg cuffs 332 are known variously in the art as gasketing cuffs, containment flaps, "stand-up" elasticized flaps, barrier cuffs, leg cuffs, leg bands, side flaps, barrier cuffs, and/or elastic cuffs. The leg cuffs may be constructed in any suitable configuration known in the art, including those described in U.S. Pat. No. 4,695,278 issued Sep. 22, 1987, and U.S. Pat. No. 4,795,454 issued Jan. 3, 1989. In FIGS. 3-4, the barrier cuff 342 is shown as being formed by a flap 344 and an elastic member 345, and the gasketing cuff 332 is shown with elastic members 333.

FIGS. 3-4 show the absorbent assembly operatively joined to a waistband 380. The absorbent assembly or any single element or subset of elements comprising the absorbent assembly may overlap the waistband 380. The absorbent assembly 322 is joined to the waistband 380 by any means known in the art including, but not limited to, ultrasonic sealing, heat sealing, pressure bonding, adhesive bonding, sewing, autogenous bonding, and the like.

The waistband 380 may encircle the waist opening 362 of the diaper 320. The waistband 380 may distribute and provide elastic resistance to the forces dynamically generated during wear. In a suitable embodiment as illustrated in FIGS. 3-4, waistband 380 may include a front waistband 380a and a back waistband 380b which may be joined by any means known in the art at a seam 342 to form a waist opening 362 and two leg openings 364. In this embodiment, the front waistband 380a and the back waistband 380b have an edge that corresponds to the front waist edge 352 and rear waist edge 354, respectively, of the diaper 320. The front waist edge 352 and rear waist edge 354 together define the waist opening 362. The absorbent assembly 322 may extend the entire longitudinal length of the front waistband 380a, the rear waistband 380b, or both. In certain embodiments, it is desirable that the absorbent core 328 does not extend into or overlap the waistband 380.

The waistband 380 may have an outer layer 392 and an inner layer 394. An elastic member 396 may be interposed between the outer layer 392 and the inner layer 394 to provide elasticity to the waistband 380. The front waistband 380a and the back waistband 380b may comprise the same materials and/or may have the same structure. Alternatively, the front waistband 380a and the back waistband 380b may comprise different materials and/or may have different structures. As shown in the embodiment of FIG. 3-4, the front waistband 380a and the back waistband 380b generally have the same structure. While the outer layer 392 and the inner layer 394 are shown as being coextensive with the front and back waistband 380a, 380b, the outer layer 392 and the inner layer 394 may differ in size or orientation (e.g., the inner layer may be smaller than the size of the front and back waistband 380a, 380b). In a suitable embodiment, either the outer layer 392 or the inner layer 394 may extend beyond the other layer. The larger layer may be folded over and, optionally, bonded to form an edge for the waistband 380.

The waistband 380 may have any shape to provide a ring-like belt. In the embodiment shown in FIG. 3-4, the waist edge 352, 354 extends laterally straight and is substantially parallel to a lower waist edge 358. Alternatively, the waist edge 352, 354 and lower waist edge 358 may be shaped, curvilinear, and/or substantially nonparallel.

The waistband 380 may comprise a variety of suitable materials. Suitable material for the waistband 380 include a wide range of substrates such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The waistband 380 may comprise a stretchable nonwoven. In a suitable embodiment, the waistband 380 has an inner layer 394 comprising a hydrophobic, non-stretchable nonwoven material, an outer layer 392 comprising a hydrophobic, non-stretchable nonwoven material, and an elastic member 396 therebetween. Construction of elastic laminates is well known in the art. Construction may comprise the elastic member attached to the facing layers while in a stretched configuration. After attachment, the elastic member is allowed to relax thereby gathering the facing layers and creating an elastic laminate. Alternatively, elastic strands or film can be attached to one or more facing layers in either a relaxed configuration or partially stretched configuration. The resulting laminate can be made stretchable (or more stretchable as in the case of partially stretch strands or film) by subjecting the laminate to an elongation process which elongates the facing layers permanently, but the elastic stands or layer only temporarily. Such processes are known in the art as "zero strain" stretch laminate formation and have been described previously. In other embodiments, the waistband 380 may comprise the inner layer 394 and/or the outer layer 392 without an elastic member 396 if sufficient elasticity is present in the material which forms the inner layer 394 and/or outer layer 392 (e.g., layer may be an elastic scrim).

The elastic member 396 may comprise one or more of elastic elements such as strands or panels extending at least in the transverse direction. The elastic member 396 may be continuously or discontinuously disposed along the transverse width of the waistband. The elastic member 396 may be disposed evenly or disproportionately along the longitudinal length of the waistband 380. As shown in FIG. 3-4, the elastic member 396 is in the form of strands continuously spanning the width of the waistband 380 and being substantially evenly spaced along the longitudinal length. It may be desirable that no elastic member 396 be provided in the portion of the waistband 380 which overlaps with the absorbent assembly 322; in such cases elastic member 396 may transversely span those portions of the waistband 380 that do not overlap the absorbent assembly 322.

As can be appreciated from the above description of suitable absorbent articles, the elastic belt 70, 370 can be manipulated to provide the desired characteristics of the present invention, such as percent recovery, open time, elongation force, and fit force. These desired characteristics may be achieved by varying the physical and compositional structure of the elastic belt 70, 370. In certain suitable embodiments, the elastic belt 70, 370 may comprise an elastic member exhibiting slow recovery characteristics. In particular embodiments, the side panels, waist feature, and/or waistband may comprise elastic members exhibiting slow recovery characteristics. An elastomer exhibits slow recovery characteristics if the material exhibits at least about 20% post elongation strain after 15 seconds of recovery at 22° C. as measured by the Post Elongation Recovery Test provided below.

A number of elastomeric polymers can be used to prepare an elastic material exhibiting slow recover characteristics. Elastomeric polymers include, but are not limited to, homopolymers (e.g., crosslinked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like.

In one embodiment, the elastomeric polymer may be a block copolymer. A number of block copolymers may be used to prepare the elastic material exhibiting slow recovery characteristics including multi-block, tapered block and star block copolymers. Generally, the block copolymers suitable for use in the slow recovery elastomer may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. Preferably, the hard block has a Tg greater than about 35° C. or is crystalline or semicrystalline with a Tm above about 35° C. The hard block portion is typically derived from vinyl monomers including vinyl arenes such as styrene and alpha-methyl-styrene or combinations thereof.

Glass transition temperatures referred to herein with reference to elastomeric polymers and the slow recovery elastomer of the present invention are determined by tensile dynamic mechanical analysis performed in the linear elastic region of the material at a frequency of 1 Hz using a temperature ramp method. Suitably, film samples with a uniform thickness of about 0.3 mm or less may be used with a temperature ramp rate of about 1° C./min or slower. The tan δ peak temperature is taken as the Tg of the particular material or phase. Crystalline melting temperatures referred to herein are determined by Differential Scanning Calorimetry using a temperature ramp rate of 10° C./min. The melting endothermic peak temperature is taken as the Tm of the particular crystalline region.

The soft block portion may be a polymer derived from conjugated aliphatic diene monomers. Typically, the soft block monomers contain fewer than about 6 carbon atoms. Suitable diene monomers include butadiene, isoprene, and the like. Suitable soft block polymers include poly(butadiene) and poly(isoprene). Suitable block copolymers for use in this invention may comprise at least one hard block (A) and at least one soft block (B). The block copolymers may have multiple blocks. In a preferred embodiment, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Also, useful in the present invention are block copolymers having more than one hard block and/or more than one soft block, wherein each hard block may be derived from the same or different monomers and each soft block may be derived from the same or different monomers.

It should be noted that where the copolymer contains residual olefinic double bonds, the copolymer may be partially or fully hydrogenated if desired. Saturation may often yield beneficial effects in the elastomeric properties of the copolymer.

The elastomeric polymer may be used in the slow recovery elastomer in an effective amount so as to achieve the desired normalized unload forces and post elongation strains. The slow recovery elastomer generally may comprise from about 20% to about 70%, preferably about 30% to about 65%, and most preferably about 45% to about 60% of the elastomeric polymer.

Elastomeric polymers may include styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S), and mixtures thereof. The block copolymers may be employed alone or in a blend of block copolymers. Suitable S-B-S and S-I-S copolymers are commercially available under the trade designation Vector® from Dexco Polymers L.P., Houston, Tex., and under the trade designation Kraton from Kraton Polymers, Houston, Tex.

Various modifying resins may be used in this slow recovery elastomer. Suitable modifying resins should preferably associate or phase mix with the soft blocks of the elastomeric polymer. While not intending to be bound by this theory, it is believed that the modifying resins raise the Tg of the soft phase to the point where molecular relaxation at the in-use temperature is slowed. The slow recovery elastomer may comprise the modifying resin in amounts from about 0% to about 60% by weight. Preferably, the composition comprises from about 20% to about 55% and even more preferably from about 40% to about 50% of the modifying resin. Suitable modifying resins useful herein may include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Preferred modifying resins also include alicyclic terpenes, hydrocarbon resins, cycloaliphatic resins, poly-beta-pinene, terpene phenolic resins, and combinations thereof. "C5 hydrocarbon resins" and "C9 hydrocarbon resins" are disclosed in U.S. Pat. No. 6,310,154.

In other suitable embodiments, the elastic belt may comprise an elastic member that is a heat shrinkable material, a water shrinkable materials, a memory visco-elastic foam, a plasto-elastic material, or combinations thereof.

Test Method

Percent Release and Percent Maximum Force

This method is used to measure the force exerted by a pull-on garment at a point of recovery after release from elongation. The force data may be used to calculate a Percent Maximum Force, which is a measure of the percent of the maximum force that is exhibited at some given point in time. The force data may be used to calculate a Percent Release, which is a measure of the change in force from some point in time compared to some later point in time. Time values are measured starting from the point in time when the gauge length, but not necessarily the sample, reaches 30% strain upon recovery from 80% strain. The zero time point corresponds to step 6 in the tensile tester program provided below.

Figure 5A:
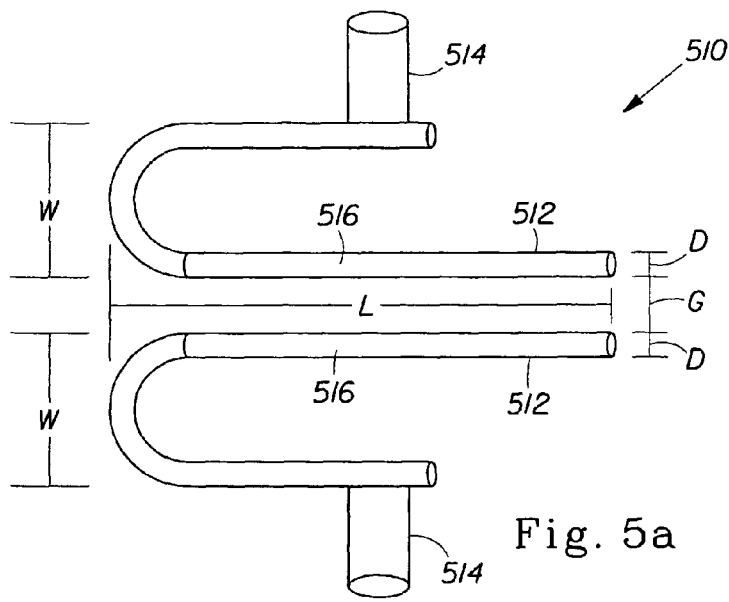
FIG. 5a shows the custom hooks used in Percent Release Test.

The percent release test is performed on a tensile tester at a constant rate of extension with a computer interface. An exemplary tester is an MTS Synergy tensile tester interfaced with Testworks 4 software. The test is conducted at ambient room conditions with a temperature of 23° C.±1° C. and a relative humidity of 50%±2%. For this test, the tensile tester is fitted with a 100N load cell and custom hook fixtures 510 as shown in FIG. 5a.

The hook fixture 510 comprises a pair J-shaped hooks 512 each with an attachment member 514. Each J-shaped hook 512 has a substantially circular cross-sectional shape with a diameter, D, of about 1 cm. The hook may have a length, L, of about 20 cm. The hook may have a width, W, of about 6 cm. The hooks 512 exhibit a smooth curvature to form the two arms that are substantially parallel to one another. The hooks 512 are formed from a material that will not interfere with the measurement of the absorbent article such as Teflon®-coated steel. Each hook 512 has an attachment member 514 that may be used to attach the hook to the tensile tester. Appropriate dimensions of the attachment member 514 may be varied to meet the needs of the tensile tester used. An engaging arm 516, the portion of the hook 512 that engages the sample, may be pivotally attached to the rest of the hook 512 such that the engaging arm 516 may rotate about its axis, which is the center of its cross-sectional face. The distance between the J-shaped hooks 512 is the gauge length, G.

The sample is measured to the nearest millimeter along the sample's waist edge to determine the circumference of the waist opening of the article. The initial gauge length G of the tensile tester is set to half of this circumference.

Figure 5B:
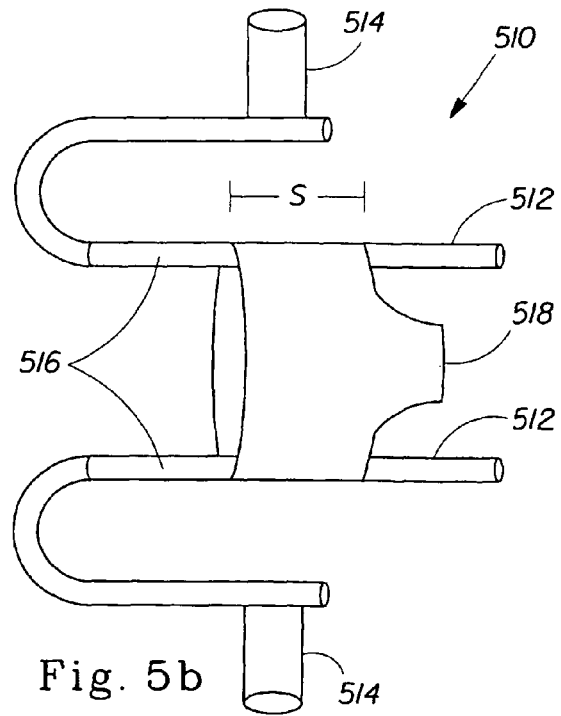
FIG. 5b shows the custom hooks used in the Percent Release Test with a sample engaged thereon.

The sample 518 is loaded onto the hooks 512 as depicted in FIG. 5b. The sample 518 is positioned so that the sample's waist edge is positioned perpendicular to the engaging arms 516 of the J-shaped hooks 512. The J-shaped hooks 512 may be inserted into the waist opening. The sides of the sample (e.g., side panel, if present) should be adjacent to the J-shaped hooks 512. The sample is slid onto the J-shaped hooks until the hooks exit the opposite side of the sample. For a pull-on diaper, one hook should enter the waist opening and exit a first leg opening and the other hooks should enter the waist opening and exit the second leg opening. The sample width, S, is the width of the portion of the sample that is in contact with the J-shaped hooks measured to the nearest millimeter.

The tensile tester may be programmed as follows:
1. The time channel is set to zero. The load channel is set to zero.
2. The gauge length is extended to 80% strain (i.e., initial gauge length is extended to a length equal to 1.8 times the initial gauge length) at a crosshead speed of 508 mm/min.
3. The sample is held at 80% strain for 10 seconds.
4. (Optional) If the sample needs to be activated, a triggering event that activates the sample is applied at the end of step 3. For example, if the sample contains a heat shrink film, sufficient heat may be applied upon the end of the 10 second hold of step 3.
5. The gauge length is reduced to 30% strain (i.e., reduced to the length equal to 1.3 times the initial gauge length) at a crosshead speed of 508 mm/min.
6. Upon return to 30% strain, the time channel is again returned to zero and force values may be recorded (see Table 1 below). The gauge length is maintained at 30% strain for three minutes.
7. Force values are recorded and plotted versus time.

Percent Release is a measure of the percent change in force over a specified unit of time. Percent release may be calculated according to the formula below where n is a time greater than 1 second:

$$\text{Percent } Release_{time=n} = \frac{(Force_{time=n} - Force_{1\ second})}{Force_{time=n}} \times 100$$

In the Percent Release calculation, times are measured from the point where the gauge length reaches 30% strain as in Step 6 above. For example, $Force_{1\ second}$ is the force recorded 1 second after the time channel is zeroed upon return of the gauge length to 30% strain.

Percent Maximum Force is a measure of the percent of the maximum force that is exhibited at some given point in time. For purposes of this measure, the term "maximum force" is the force measured at 180 seconds after the time channel has been reset to zero in Step 6 according to the Test Method presented above. Percent Maximum Force may be calculated according to the formula below where n is time:

$$\text{Percent Maximum } Force_{time=n} = \frac{Force_{time=n}}{Force_{time=180\ seconds}} \times 100$$

30% Recovery Time

The 30% Recovery Time is a measure of the time it takes for a pull-on diaper to return to 30% strain after release from an elongation of 80% strain. For purposes of this calculation, the sample is considered to have returned to 30% once a measurable force is exerted by the sample and recorded by the tensile tester (Step 7 in the method provided above). The 30% recovery time is the time at which a force is exerted by the sample onto the hooks. The 30% Recovery Time can be considered a quantitative measure of the qualitative phenomena of "snap-back." Samples exhibiting low 30% Recovery Times may be considered fast in that the sample recovers to 30% strain instantaneously (i.e., generally considered a time less than about 1 second) after release from an elongating force at 80% strain. Conversely, samples exhibiting higher 30% Recovery Times can be considered slow in that the sample recovers to 30% strain over time (i.e., generally considered a time greater than about 1 second). Furthermore, since time zero begins once the gauge length returns to 30% strain, a sample that exhibits a force at time zero may be considered to have recovered at least as fast as that of the gauge speed of the tensile tester. Since the gauge speed on return from 80% strain to 30% strain is 508 mm/min, samples exhibiting a force at time zero are considered to exhibit a recovery speed of 508 mm/min or faster.

Post Elongation Recovery Test Method for Elastomers

This method is used to determine the post elongation strain of an elastomer as a function of temperature and time. This method includes stretch method and a recovery method. The measurement may be done at 22° C. (72° F.) or at 32° C. (90° F.). The method employs a Dynamic Mechanical Analyzer (DMA) such as a TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis. Many other types of DMA devices exist, and the use of dynamic mechanical analysis is well known to those skilled in the art of polymer and copolymer characterization.

Methods of operation and calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The DMA 2980 is set to the Controlled Force Mode with the film clamp. The film clamp is mounted onto the DMA 2980 and calibrated according to the User's Reference Guide. The material to be tested is cut into samples of substantially uniform dimension. Appropriate sample dimensions may be selected to achieve the required strain. For the DMA 2980, suitable sample dimensions are approximately 6.4 mm wide by approximately 0.15 mm thick. The floating film clamp of the DMA 2980 is adjusted to a position which provides approximately 6 mm between the clamping surfaces, and is locked in this position. The sample is mounted in the film clamps and the lower clamp is allowed to float to allow determination of the actual gauge length which exists between the film clamps.

Stretch Method—Specific DMA 2980 parameter settings for the above sample dimensions are set as follows: Preload force applied to sample in clamp (0.01N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$ (3) Data Storage ON, and (4) Ramp Force 5.0 N/min to 18.0 N.

Upon initiation of the test, the temperature ramps to the specified $T_i$ (22° C. or 32° C.) [method segment 1] and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 5 N per minute to approximately 30 mm in length. The sample is locked in place at the stretched length of approximately 30 mm and maintained at $T_i$. The force required to reach the 400% strain is recorded manually from the digital readout on the instrument.

For samples of different dimensions, the applied force is adjusted to achieve an applied ramp force of 5 N/min per square millimeter of initial sample cross-sectional area, and the maximum displacement is adjusted to achieve a strain of 400%. The percent strain is calculated by subtracting the gauge length from the stretched length, then dividing the result by the gauge length and multiplying by 100. A sample stretched from an initial length of 6 mm to a length of 30 mm results in a 400% strain.

Recovery Method—The Recovery Method is loaded onto the instrument and initiated 15 seconds after reaching the desired strain (400%) in the Stretch Method. The four segments of the recovery method are (1) Data Storage ON, (2) Force 0.01N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature may be recorded as a function of recovery time.

EXAMPLES

Examples 1 and 2

These examples are of an illustrative waistband that may be used in the diaper depicted in FIGS. 3-4. The waistband may be constructed as follows:

1) An elastomeric film may be compounded comprising about 45% Vector 4211 available from Dexco Polymers L.P., Houston, Tex., 45% poly(t-butylstyrene), and 10% mineral oil. The poly(t-butylstyrene) is ideally of approximately 12 kDa weight average molecular weight. The elastomeric film was subjected to aging. The film used in Examples 1 and 2 were aged at least 24 months.
2) The elastomer film may be resized into substantially rectangular bands having a length of 120 mm, a width of 5 mm, and a thickness of about 0.14 mm to about 0.17 mm. The bands may be elongated to 600 mm (i.e., 400% strain) and bonded to a first substrate. The first substrate may be from 620-660 mm in length and may be from 70-120 mm in width, preferably 70 mm. The first substrate may be a commercial nonwoven such as supplier code H0201010 available from Fibertex A/S, Aalborg, Denmark. Approximately 14 bands of 5 mm wide elastomer film may be adhered to the first substrate by use of an adhesive such as H2031 available from Bostik Findley, Middleton, Mass. An adhesive laydown of approximately 30 g/m² on the first substrate is sufficient. The bands are evenly distributed across the width of the first substrate. In their elongated state, the bands extend substantially the length of the first substrate and are substantially parallel to the longest edge of the substrate.
3) A second substrate is bonded, by use of a second application of adhesive, to the first substrate such that the bands are positioned therebetween. Ideally, the second substrate may be the same as the first substrate (i.e., same dimensions and composition). A second application of adhesive (i.e., H2031) may be applied to the first substrate/band laminate. The resulting stretch laminate is compressed using a hand roller.
4) Two stretch laminates may be formed according to steps 1-3. The two stretch laminates may be placed is a face-to-face relationship such that the two laminates fully overlap. The two laminates are bonded to one another along their shortest distal edges. The bonding area may extend anywhere from about 5 mm to about 15 mm in width as measured along the longest edge of the laminate. The two laminates may be bonded together with an adhesive such as H2031 with a laydown of 30 g/m².
5) The two bonded stretch laminates result in a waistband having a circumference of about 300-380 mm. Example 1 had a circumference of about 306 mm. Example 2 had a circumference of about 360 mm.

An absorbent assembly may be attached to the waistband to yield an absorbent article substantially similar to the one depicted in FIGS. 3-4. Absorbent assembly construction is well known in the art. Ideally, the absorbent assembly will be bonded to the waistband so as to minimize the amount of overlap between the absorbent assembly and the waistband. Examples 1 and 2 may be constructed according to the steps provided above. Example 1 differs from Example 2 in circumference. Example 1 had a circumference of about 306 mm and Example 2 had a circumference of about 360 mm.

Examples 3 and 4

These examples are comparative examples using a Pampers® Easy Up size 2T-3T, available from The Procter & Gamble Company, Cincinnati, Ohio.

Example 5 and 6

These examples are comparative examples using a Huggies Pull-Ups® boys size 3T-4T, available from Kimberly-Clark Corp., Neenah, Wis.

Example 7 and 8

These examples are comparative examples using a Huggies Pull-Ups® girls size 3T-4T, available from Kimberly-Clark Corp., Neenah, Wis.

Test Results

Provided below in Tables 1 and 2 are the results of the Percent Release Test for Examples 1-8. Table 1 lists the raw force values for the Examples at discrete points in time. Table 2 shows the forces of Table 1 normalized and rounded to the nearest $\frac{1}{100}^{th}$ decimal place. Normalization may be performed by taking the raw force values for the Examples at various points in time (as provided in Table 1) and dividing by the width of the sample. The force values are considered accurate to plus or minus 0.05 N. As a result, the negative force value for Example 1 at the time of 1 second is believed to be a signal-to-noise artifact and, given the accuracy of the measurement may correspond to no force at the time of 1 second. Likewise, the force value for Example 2 at the time of 1 second may also correspond to no force. As can be seen from the data of Table 1, the present invention (Examples 1-2) exhibits a recovery where the forces gradually build to the maximum force as measured at the time of 180 seconds. The comparative examples (Examples 3-8) show that the force values are high at the start of the measurement cycle and increases slightly after a 15-30 seconds time.

TABLE 1

Forces (N)

| | Time | | | | | | | |
|---|---|---|---|---|---|---|---|---|
| | 1 | 15 | 30 | 45 | 60 | 90 | 120 | 180 |
| Example 1 | −0.02 | 0.15 | 0.45 | 0.69 | 0.84 | 1.10 | 1.24 | 1.35 |
| Example 2 | 0.03 | 0.21 | 0.52 | 0.72 | 0.87 | 1.13 | 1.26 | 1.36 |
| Example 3 | 2.50 | 3.26 | 3.39 | 3.45 | 3.51 | 3.53 | 3.57 | 3.56 |
| Example 4 | 2.57 | 3.25 | 3.40 | 3.48 | 3.52 | 3.54 | 3.59 | 3.61 |
| Example 5 | 4.46 | 5.05 | 5.17 | 5.22 | 5.25 | 5.28 | 5.31 | 5.30 |
| Example 6 | 4.15 | 4.71 | 4.83 | 4.88 | 4.89 | 4.94 | 4.94 | 4.95 |
| Example 7 | 4.94 | 5.59 | 5.70 | 5.76 | 5.79 | 5.80 | 5.82 | 5.81 |
| Example 8 | 4.85 | 5.42 | 5.53 | 5.57 | 5.59 | 5.62 | 5.63 | 5.63 |

TABLE 2

Forces (N/cm)

| | Width (mm) | Time (s) | | | | | | | |
|---|---|---|---|---|---|---|---|---|---|
| | | 1 | 15 | 30 | 45 | 60 | 90 | 120 | 180 |
| Example 1 | 70 | 0.00 | 0.02 | 0.06 | 0.10 | 0.12 | 0.16 | 0.18 | 0.19 |
| Example 2 | 70 | 0.00 | 0.03 | 0.07 | 0.10 | 0.12 | 0.16 | 0.18 | 0.19 |
| Example 3 | 89 | 0.28 | 0.37 | 0.38 | 0.39 | 0.39 | 0.40 | 0.40 | 0.40 |
| Example 4 | 89 | 0.29 | 0.37 | 0.38 | 0.39 | 0.40 | 0.40 | 0.40 | 0.41 |
| Example 5 | 110 | 0.41 | 0.46 | 0.47 | 0.47 | 0.48 | 0.48 | 0.48 | 0.48 |
| Example 6 | 110 | 0.38 | 0.43 | 0.44 | 0.44 | 0.44 | 0.45 | 0.45 | 0.45 |
| Example 7 | 110 | 0.45 | 0.51 | 0.52 | 0.52 | 0.53 | 0.53 | 0.53 | 0.53 |
| Example 8 | 110 | 0.44 | 0.49 | 0.50 | 0.51 | 0.51 | 0.51 | 0.51 | 0.51 |

Table 3 provides the percent maximum forces for the various examples at discrete points in time. The percent maximum force for a given time is computed by taking the force measurement at some time and dividing by the force at time=180 second and multiplying by 100. As used herein, the term "maximum force" refers to the force, either raw or normalized, measured for a sample at 180 seconds. This percent maximum force value can be used to show how quickly it takes for the sample to approach its maximum force value and relatively how much force is exerted.

Figure 6:
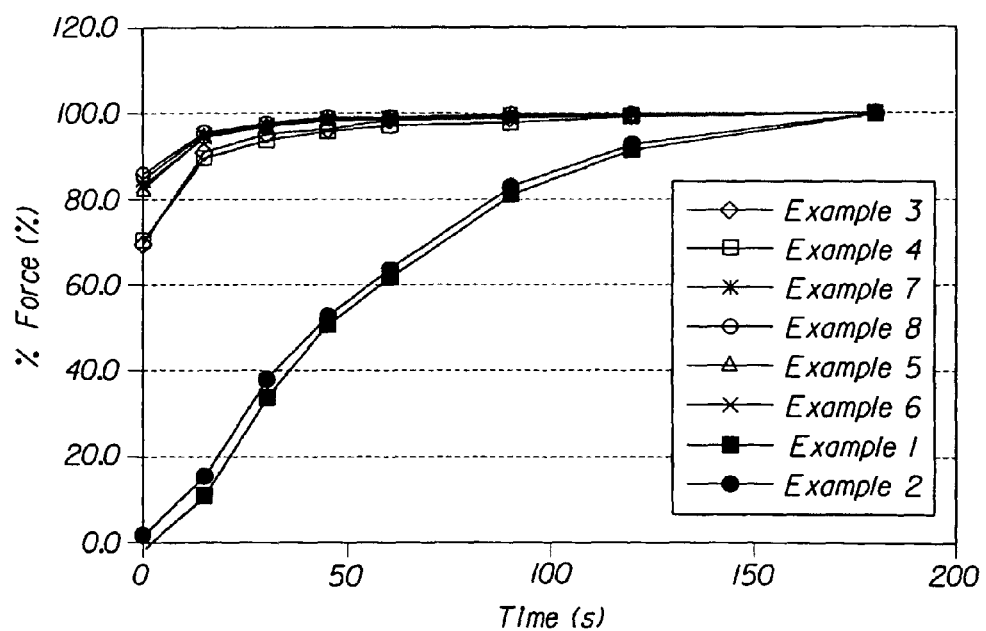
FIG. 6 is a graph plotting the Percent Maximum Force versus time for the Examples.

FIG. 6 is a graph that incorporates the data from Table 3 with the Percent Maximum Force being plotted versus time. As may be appreciated from Table 3 and/or FIG. 6, the present invention (Examples 1 and 2) exhibit a slow build in force to reach the maximum force. Conversely, the comparative examples (Examples 3-8) exhibit relatively instantaneous (e.g., as measured at time=1 second) exertion of a large percent (i.e., 70% or more) of the maximum force. Furthermore, by 15 seconds, the comparative examples are exhibiting at least 90% of their maximum force whereas the present invention is exhibiting only about 11-15% of its maximum force. Qualitatively, the present invention does not exhibit the "snap back" present in the comparative examples. When viewed in relation to a child self-applying a pull-on diaper, low initial force (i.e., a low percent maximum force at the lower time values) means that the child may extend the waist opening of the pull-on diaper without much effort. It is believed that a pull-on diaper exhibiting lower initial forces is easier to apply by a child with or without caregiver assistance.

TABLE 3

Percent Maximum Force (%)

| | Time (s) | | | | | | | |
|---|---|---|---|---|---|---|---|---|
| | 1 | 15 | 30 | 45 | 60 | 90 | 120 | 180 |
| Example 1 | −1 | 11 | 33 | 51 | 62 | 81 | 92 | 100 |
| Example 2 | 2 | 15 | 38 | 53 | 64 | 83 | 93 | 100 |
| Example 3 | 70 | 92 | 95 | 97 | 99 | 99 | 100 | 100 |
| Example 4 | 71 | 90 | 94 | 96 | 98 | 98 | 99 | 100 |
| Example 5 | 84 | 95 | 98 | 98 | 99 | 100 | 100 | 100 |
| Example 6 | 84 | 95 | 98 | 99 | 99 | 100 | 100 | 100 |
| Example 7 | 85 | 96 | 98 | 99 | 100 | 100 | 100 | 100 |
| Example 8 | 86 | 96 | 98 | 99 | 99 | 100 | 100 | 100 |

Table 4 shows the percent release values for each of the Examples. The equation for calculating Percent Release is presented above. As may be appreciated from the percent release calculation, Percent Release values approaching zero indicate that the force at time=n has not increased appreciably compared to the force at time=1 second. Likewise, a percent release value approaching 100 indicates that the force at time=n has increased appreciably compared to the force at time=1 second.

TABLE 4

Percent Release (%)

| | Time (s) | | | | | | |
|---|---|---|---|---|---|---|---|
| | 15 | 30 | 45 | 60 | 90 | 120 | 180 |
| Example 1 | 112.6 | 104.1 | 102.7 | 102.2 | 101.7 | 101.5 | 101.4 |
| Example 2 | 83.7 | 93.5 | 95.3 | 96.1 | 97.0 | 97.3 | 97.5 |
| Example 3 | 23.3 | 26.2 | 27.5 | 28.6 | 29.1 | 30.0 | 29.6 |
| Example 4 | 21.0 | 24.5 | 26.2 | 26.9 | 27.4 | 28.5 | 28.8 |
| Example 5 | 11.8 | 13.8 | 14.6 | 15.1 | 15.7 | 16.1 | 16.0 |
| Example 6 | 11.8 | 14.0 | 14.9 | 15.0 | 16.0 | 15.8 | 16.1 |
| Example 7 | 11.6 | 13.2 | 14.2 | 14.6 | 14.8 | 15.1 | 14.8 |
| Example 8 | 10.5 | 12.1 | 12.9 | 13.2 | 13.7 | 13.8 | 13.8 |

Figure 7:
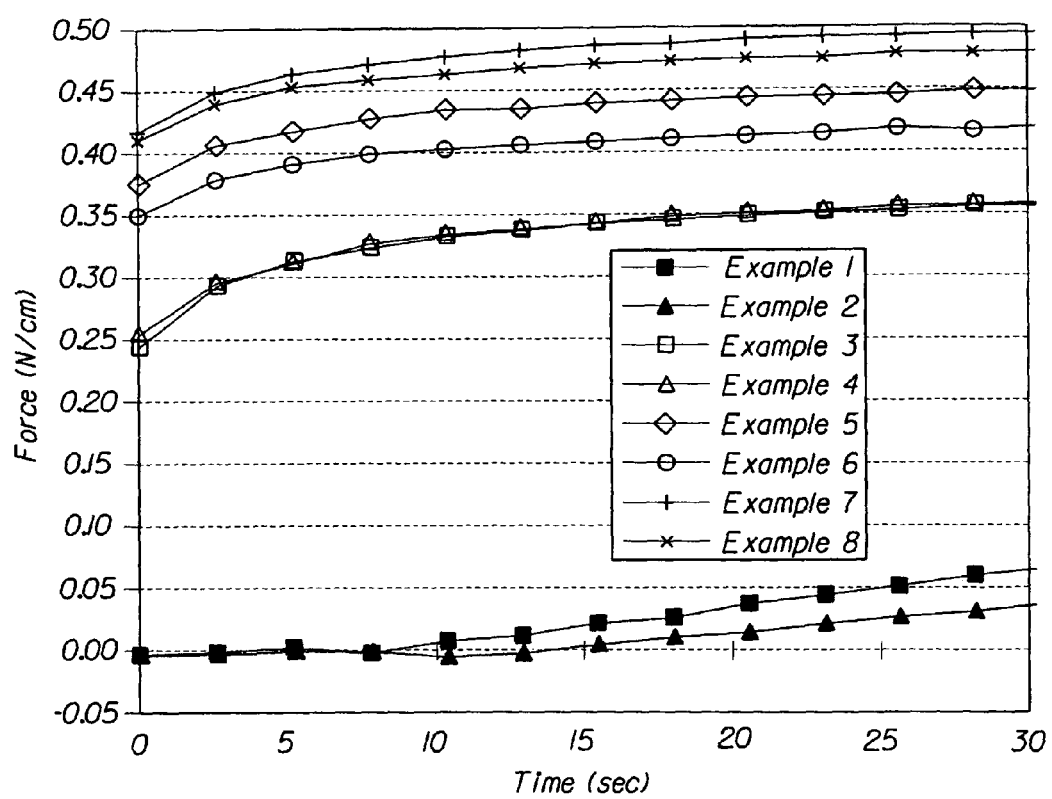
FIG. 7 is a graph plotting the normalized force versus time for the Examples.

FIG. 7 is a plot of the normalized forces versus time for Examples 1-8. As can be seen from the graph, the comparative examples (Examples 3-8) illustrate that a force is being applied to the hooks at time=0 seconds. As a result, Examples 3-8 each exhibit a 30% Recovery Time of 0 seconds. Conversely, as shown in FIG. 7, the present invention (Examples 1-2) exhibits a 30% Recovery Time of between approximately 7.5 seconds and 12.5 seconds. It is believed that the 30% Recovery Times exhibited by the present invention results in the waist opening maintaining an enlarged state during application of the pull-on diaper. Consequently, the 30% Recovery Time exhibited by the present invention may allow for easier application of a pull-on diaper.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pull-on diaper having a wearer-faceable surface; a longitudinal centerline and a lateral centerline; a front waist region, a back waist region, and a crotch region disposed between the front and back waist regions, wherein the front waist region and back waist region are joined to form a waist opening and leg openings; the pull-on diaper comprising an absorbent assembly and an elastic belt;
   wherein the absorbent assembly comprises a liquid pervious topsheet, a liquid impervious backsheet, and an absorbent core disposed between the topsheet and backsheet;
   wherein the elastic belt exhibits less than about 80% of the maximum force after 15 seconds as measured by the Percent Release Test;
   wherein the elastic belt comprises a plurality of elastic strands that each include a slow recovery elastomer that are stretch bonded between the topsheet and the backsheet, the slow recovery elastomer comprising between about 40% and about 50% of a modifying resin; and
   wherein the modifying resin raises a glass transition temperature of a soft phase of an elastomeric polymer.

2. The disposable pull-on diaper of claim 1 wherein the elastic belt exhibits less than about 50% of the maximum force after 15 seconds as measured by the Percent Release Test.

3. The disposable pull-on diaper of claim 1 wherein the elastic belt exhibits less than about 20% of the maximum force after 15 seconds as measured by the Percent Release Test.

4. The disposable pull-on diaper of claim 1 wherein the elastic belt exhibits less than about 90% of the maximum force after 45 seconds as measured by the Percent Release Test.

5. The disposable pull-on diaper of claim 1 wherein the elastic belt exhibits less than about 70% of the maximum force after 45 seconds as measured by the Percent Release Test.

6. The disposable pull-on diaper of claim 1 wherein the elastic belt exhibits less than about 55% of the maximum force after 45 seconds as measured by the Percent Release Test.

7. The disposable pull-on diaper of claim 1 wherein the elastic belt further exhibits a 30% Recovery Time of at least 0.1 second.

8. The disposable pull-on diaper of claim 1 wherein the elastic belt further exhibits a 30% Recovery Time of at least 1 second.

9. The disposable pull-on diaper of claim 1 wherein the elastic belt further exhibits a 30% Recovery Time of at least 5 seconds.

10. The disposable pull-on diaper of claim 1 wherein the elastic belt further exhibits a 30% Recovery Time of at least 10 seconds.

11. The disposable pull-on diaper of claim 1 wherein the elastic belt exhibits a recovery speed of less than about 508 mm/min.

12. The disposable pull-on diaper of claim 1 wherein the elastic belt further exhibits a maximum normalized force of at least about 0.15 N/cm as measured by the Percent Release Test.

13. The disposable pull-on diaper of claim 1 wherein the elastic belt further exhibits at least about 30% release after 180 seconds as measured by the Percent Release Test.

14. The disposable pull-on diaper of claim 1 wherein the elastic belt further exhibits at least about 60% release after 180 seconds as measured by the Percent Release Test.

15. The disposable pull-on diaper of claim 1 wherein the elastic belt further exhibits at least about 90% release after 180 seconds as measured by the Percent Release Test.

16. The disposable pull-on diaper of claim 1 wherein the slow recovery elastomer includes an elastomeric polymer selected from the group consisting of styrenic block copolymers, natural and synthetic rubbers, polyisoprene, neoprene, polyurethanes, silicone rubbers, hydrocarbon elastomers, ionomers, and combinations thereof.

17. The disposable pull-on diaper of claim 16 wherein the elastomeric polymer is a block copolymer comprising a soft block and at least one substantially hard block.

18. The disposable pull-on diaper of claim 1 wherein the modifying resin is selected from the group consisting of unhydrogenated C5 hydrocarbon resins; C9 hydrocarbon resins; partially and fully hydrogenated C5 hydrocarbon resins; C9 hydrocarbon resins; cycloaliphatic resins; terpene resins; poly(t-butylstyrene) and oligomers thereof; rosin and rosin derivatives; coumarone indenes; polycyclopentadiene and oligomers thereof; phenolic resins; indene polymers, oligomers and copolymers; acrylate and methacrylate oligomers, polymers, and copolymers; and combinations thereof.

19. The disposable pull-on diaper of claim 1 wherein the slow recovery elastomer exhibits at least about 20% post elongation strain after 15 seconds of recovery at 22° C.

* * * * *